US012239754B2

(12) United States Patent
Knatt et al.

(10) Patent No.: US 12,239,754 B2
(45) Date of Patent: Mar. 4, 2025

(54) SANITIZING CABINET

(71) Applicant: True Manufacturing Co., Inc., O'Fallon, MO (US)

(72) Inventors: Kevin Knatt, St. Louis, MO (US); John Friend, O'Fallon, MO (US); Edward Hartman, O'Fallon, MO (US); Steven Trulaske, O'Fallon, MO (US)

(73) Assignee: TRUE MANUFACTURING CO. INC, O'Fallon, MO (US)

( * ) Notice: Subject to any disclaimer, the term of this patent is extended or adjusted under 35 U.S.C. 154(b) by 816 days.

(21) Appl. No.: 17/244,553

(22) Filed: Apr. 29, 2021

(65) Prior Publication Data

US 2022/0143245 A1 May 12, 2022

Related U.S. Application Data

(60) Provisional application No. 63/171,874, filed on Apr. 7, 2021, provisional application No. 63/017,518, filed on Apr. 29, 2020.

(51) Int. Cl.
*A61L 2/20* (2006.01)
*A61L 2/24* (2006.01)
*A61L 101/02* (2006.01)

(52) U.S. Cl.
CPC ............ *A61L 2/202* (2013.01); *A61L 2/24* (2013.01); *A61L 2101/02* (2020.08);
(Continued)

(58) Field of Classification Search
None
See application file for complete search history.

(56) References Cited

U.S. PATENT DOCUMENTS 5,266,275 A 11/1993 Faddis
5,868,999 A 2/1999 Karlson
(Continued)

FOREIGN PATENT DOCUMENTS

EP 1500404 A1 1/2005
EP 2273004 A1 1/2011
(Continued)

OTHER PUBLICATIONS

International Search Report and Written Opinion from PCT/US2021/029921, mailed Sep. 28, 2021, 22 pages.

*Primary Examiner* — Jennifer A Leung
(74) *Attorney, Agent, or Firm* — Stinson LLP

(57) ABSTRACT

A sanitizing cabinet system includes ozone distribution passaging in open fluid communication with a sanitizing compartment inside a cabinet. An ozone generator and a sanitizing air mover are located in the ozone distribution passaging. The sanitizing air mover moves air from the sanitizing compartment across the generator to form ozonated air and moves the ozonated air from the ozone distribution passaging into the sanitizing compartment. A control system controls the ozone generator and air mover based on feedback from an ozone sensor indicating ozone exposure over time. An ozone conversion device is mounted on a dividing wall of the cabinet outside the sanitizing compartment. The dividing wall has inlet and outlet holes, and the ozone conversion device has upstream and downstream chambers in communication with the inlet and outlet holes. Selectively openable dampers separate upstream and downstream chambers from an ozone conversion chamber in which ozone conversion catalyst is received.

19 Claims, 24 Drawing Sheets

(52) U.S. Cl.
CPC ...... *A61L 2202/11* (2013.01); *A61L 2202/122* (2013.01); *A61L 2202/13* (2013.01); *A61L 2202/14* (2013.01); *A61L 2202/15* (2013.01)

(56) References Cited

U.S. PATENT DOCUMENTS

| | | | |
|---|---|---|---|
| 7,056,476 B2 | 6/2006 | Okada et al. |
| 7,114,637 B2 | 10/2006 | Davis |
| 7,128,872 B2 | 10/2006 | Robitaille et al. |
| 7,189,349 B2 | 3/2007 | Karle |
| 7,272,947 B2 | 9/2007 | Anderson et al. |
| 7,358,803 B2 | 4/2008 | Goldberg et al. |
| 7,401,469 B2 | 7/2008 | Joshi et al. |
| 7,582,257 B2 | 9/2009 | Bedard et al. |
| 7,604,774 B2 | 10/2009 | Mole et al. |
| 7,608,217 B2 | 10/2009 | Champagne |
| 7,654,102 B2 | 2/2010 | Hurlebaus et al. |
| 7,655,150 B2 | 2/2010 | Davis |
| 7,824,480 B2 | 11/2010 | Hurlebaus et al. |
| 7,886,557 B2 | 2/2011 | Anderson et al. |
| 8,056,358 B1 | 11/2011 | Shelton |
| 8,343,341 B2 | 1/2013 | Davis et al. |
| 8,354,057 B2 | 1/2013 | Heselton et al. |
| 8,366,920 B2 | 2/2013 | Davis |
| 8,465,704 B2 | 6/2013 | Watson et al. |
| 8,617,479 B2 | 12/2013 | Gil et al. |
| 8,624,202 B2 | 1/2014 | Gil |
| 8,647,501 B2 | 2/2014 | Davis |
| 8,696,985 B2 | 4/2014 | Gil et al. |
| 8,784,731 B2 | 7/2014 | Gil et al. |
| 8,865,065 B2 | 10/2014 | Kain et al. |
| 8,871,085 B2 | 10/2014 | Davis |
| 8,919,356 B2 | 12/2014 | Brockman et al. |
| 9,011,787 B2 | 4/2015 | Dunkley et al. |
| 9,072,804 B2 | 7/2015 | Dunkley et al. |
| 9,078,941 B2 | 7/2015 | Dunkley et al. |
| 9,186,428 B2 | 11/2015 | Jennings |
| 9,233,182 B2 | 1/2016 | Arlemark |
| 9,327,040 B2 | 5/2016 | Kain et al. |
| 9,375,500 B2 | 6/2016 | Dunkley et al. |
| 9,446,968 B2 | 9/2016 | Davis |
| 9,480,267 B2 | 11/2016 | Arrigo |
| 9,497,977 B2 | 11/2016 | Biotti et al. |
| 9,801,967 B2 | 10/2017 | Wiget et al. |
| 10,111,973 B2 | 10/2018 | Thorn et al. |
| 10,143,763 B2 | 12/2018 | Campalans et al. |
| 10,300,161 B2 | 5/2019 | Erbs |
| 10,520,239 B2 | 12/2019 | Chezem et al. |
| 10,555,548 B2 | 2/2020 | Smith |
| 10,591,198 B2 | 3/2020 | Abeygunawardana et al. |
| 10,596,402 B2 | 3/2020 | Moore et al. |
| 10,597,317 B1 | 3/2020 | Lynn |
| 10,900,703 B2 | 1/2021 | Biotti et al. |
| 11,253,620 B2 | 2/2022 | Golkowski et al. |
| 11,305,990 B2 | 4/2022 | Naito |
| 11,365,485 B2 | 6/2022 | Bahar et al. |
| 2004/0028583 A1* | 2/2004 | Hedman ............ A61L 2/06 422/123 |
| 2010/0196194 A1 | 8/2010 | Voeten et al. |
| 2010/0288710 A1 | 11/2010 | Davis |
| 2011/0110820 A1 | 5/2011 | Mann |
| 2016/0115644 A1* | 4/2016 | Cho ............ D06F 58/20 34/212 |
| 2016/0235875 A1* | 8/2016 | Schmidt ............ A61L 2/26 |
| 2017/0210623 A1 | 7/2017 | Lynn |
| 2018/0207307 A1 | 7/2018 | Schwartz et al. |
| 2019/0175773 A1 | 6/2019 | Erbs |
| 2019/0269809 A1 | 9/2019 | Grajcar |
| 2020/0384142 A1 | 12/2020 | Medvedev et al. |
| 2021/0268136 A1 | 9/2021 | Engler et al. |

FOREIGN PATENT DOCUMENTS

| | | | |
|---|---|---|---|
| EP | 1500404 B1 | 3/2011 | |
| EP | 3892307 A1 | 12/2020 | |
| EP | 3900747 A1 | 10/2021 | |
| EP | 3900747 A4 | 10/2021 | |
| EP | 3900747 A8 | 12/2021 | |
| JP | 07227322 A | 8/1995 | |
| JP | 09253180 A | 9/1997 | |
| KR | 200318972 Y1 * | 7/2003 | |
| RU | 2604967 C1 * | 12/2016 | |
| WO | WO-2014060051 A1 * | 4/2014 | ............ A61L 2/10 |
| WO | 2017132146 A1 | 8/2017 | |
| WO | 2019144131 A1 | 7/2019 | |
| WO | 2019156679 A1 | 8/2019 | |
| WO | 2022107045 A1 | 5/2022 | |

\* cited by examiner

Replacement Schedule

| | CYCLE MAX | PERFORMANCE | ACTION |
|---|---|---|---|
| Sanitizing Bulb | 5,000 | 80% | alarm |
| Catalytic Converter | 20,000 | 70% | notify |
| Door Lock/Gaskets | 50,000 | N/A | alarm |

[Conservative] [Standard] [Extended]

FIG. 25

Replacement Schedule

| | CYCLE MAX | PERFORMANCE | ACTION |
|---|---|---|---|
| Sanitizing Bulb | 10,000 | 70% | alarm |
| Catalytic Converter | 50,000 | 60% | notify |
| Door Lock | 100,000 | N/A | alarm |

[Conservative] [Standard] [Extended]

FIG. 26

SANITIZING CABINET

CROSS-REFERENCE TO RELATED APPLICATIONS

This Application claims priority to U.S. Provisional Patent Application Ser. No. 63/017,518, filed Apr. 29, 2020, and U.S. Provisional Patent Application Ser. No. 63/171,874, filed Apr. 7, 2021, each of which is hereby incorporated by reference in its entirety.

FIELD

The present disclosure generally relates to a sanitizing cabinet system.

BACKGROUND

Various technologies exist for sanitizing articles. For example, some sanitizing devices use direct UV light to sanitize the exposed surface of one or more articles. Other sanitizing devices apply chemical disinfectants or detergents. Still other sanitizing devices utilize electrostatic cleaning to drive sanitizing action. Yet another mode of sanitization can be achieved by directing ozone or ozonated air over the articles to be sanitized.

SUMMARY

In one aspect, a sanitizing cabinet system comprises a cabinet defining a sanitizing compartment, ozone distribution passaging in open fluid communication with the sanitizing compartment, an ozone generator in the ozone distribution passaging, and a sanitizing air mover in the ozone distribution passaging configured to move air from the sanitizing compartment across the ozone generator to form ozonated air and to move the ozonated air into the sanitizing compartment.

In another aspect, an ozone conversion device for selectively converting ozone in a sanitizing compartment of a sanitizing cabinet system comprises a housing defining an interior space. First and second dampers are in the housing. The first and second dampers are configured to divide the interior space of the housing between an upstream chamber, an ozone conversion chamber, and a downstream chamber. The first and second dampers are configured to be selectively opened and closed. The first and second dampers are configured to fluidly separate the ozone conversion chamber from the upstream chamber and the downstream chamber when closed and configured to provide fluid communication between the ozone conversion chamber and the upstream chamber and the downstream chamber when opened. An ozone conversion catalyst is in the ozone conversion chamber. An ozone conversion air mover is in the housing. The housing is configured to mount on a wall of a sanitizing cabinet system such that the upstream chamber fluidly communicates with an inlet opening formed in the wall and the downstream chamber fluidly communicates with an outlet opening formed in the wall.

In another aspect, a sanitizing cabinet system comprises a cabinet defining a sanitizing compartment, an ozone generator configured to generate ozone in the sanitizing compartment, an ozone sensor configured to output a signal representative of a concentration of ozone in the sanitizing compartment, and a controller connected to the ozone generator and the ozone sensor. The controller is configured to execute sanitizing cycles in which the controller maintains the ozone generator in an operating state until the controller determines, based on an evaluation of the signal from the ozone sensor with respect to time, that an amount of ozone exposure inside the sanitizing compartment has reached an exposure threshold.

In another aspect, a method of using a sanitizing cabinet system comprises transmitting, by a controller of the sanitizing cabinet system, to a remote monitoring system, an indication of a number of cycles in which an expendable part has been used in the sanitizing cabinet system without replacement. The controller receives from the remote monitoring system a command signal responsive to said transmitted indication of the number of cycles. The command signal provides a command to lock the sanitizing cabinet system. In response to receiving the command signal, the controller switches the sanitizing cabinet system from an operational state to a locked state.

In another aspect, a sanitizing cabinet system comprises a cabinet defining a sanitizing compartment, a door for selectively opening and closing the sanitizing compartment, an automatic door lock for selectively locking and unlocking the door in a closed position, and an ozone generator configured to generate ozonated air. The sanitizing cabinet is configured to direct the ozonated air generated by the ozone generator into the sanitizing compartment. A controller and/or interlock is configured to maintain the sanitizing fluid generator in an off state unless the automatic door lock locks the door in the closed position.

In another aspect, a method of repurposing existing cabinet inventory including parts assembled into or capable of being assembled into a cabinet comprises mounting an ozone generator on the cabinet such that the ozone generator is received in air distribution passaging of the cabinet through which air is configured to be distributed throughout a closable storage compartment of the cabinet. An ozone conversion device is fluidly connected to the cabinet.

Other aspects will be in part apparent and in part pointed out hereinafter.

BRIEF DESCRIPTION OF THE DRAWINGS

FIG. 25 is an exemplary screenshot of a replacement schedule view for a set of expendable parts of the sanitizing cabinet system including a series of selection items enabling user selection of a replacement schedule;

FIG. 26 is an exemplary screenshot of the replacement schedule view of FIG. 25 in another configuration;

Corresponding reference characters indicate corresponding parts throughout the drawings.

DETAILED DESCRIPTION

Figure 1:
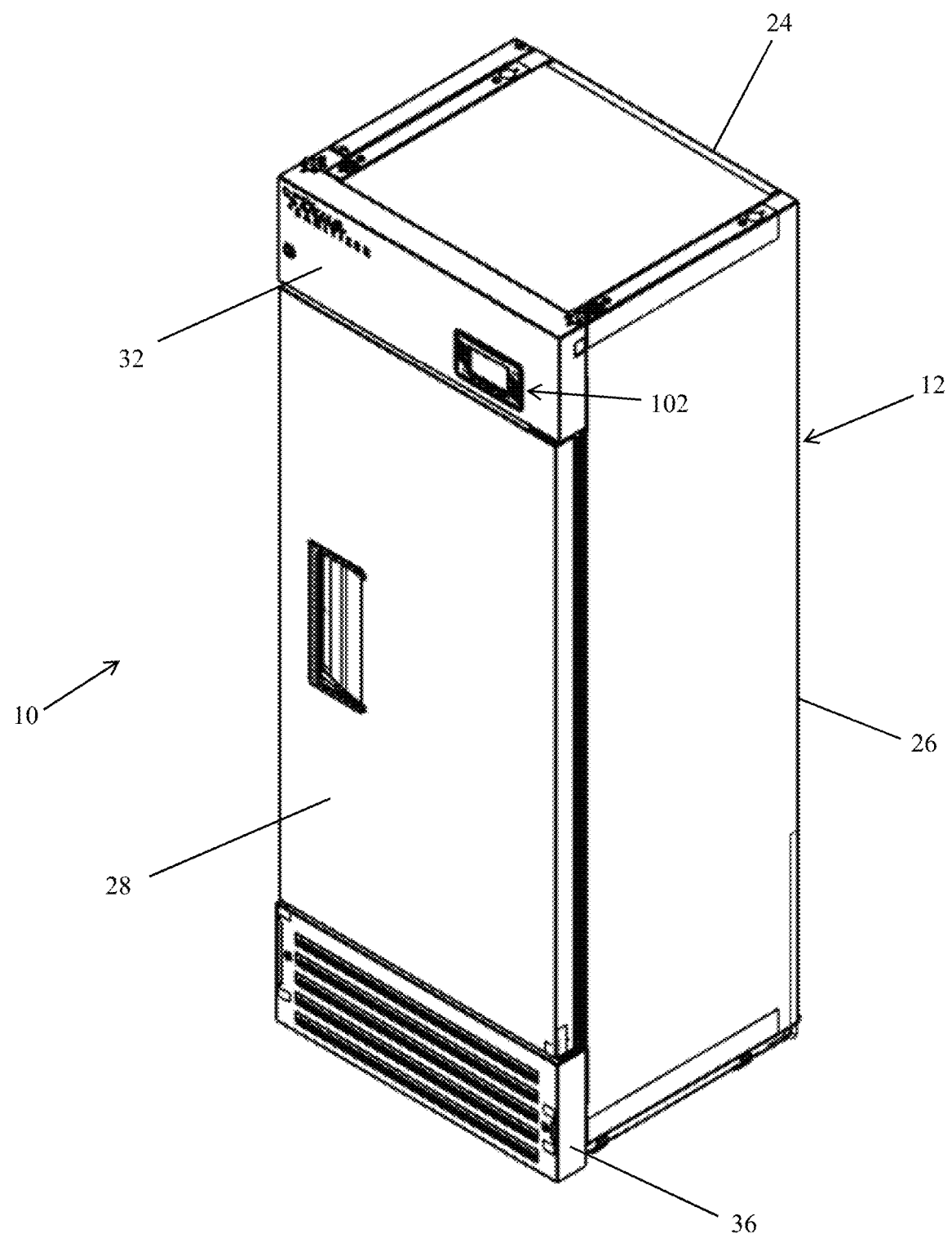
FIG. 1 is a perspective of an exemplary embodiment of a sanitizing cabinet system in accordance with the present disclosure.
Figure 2:
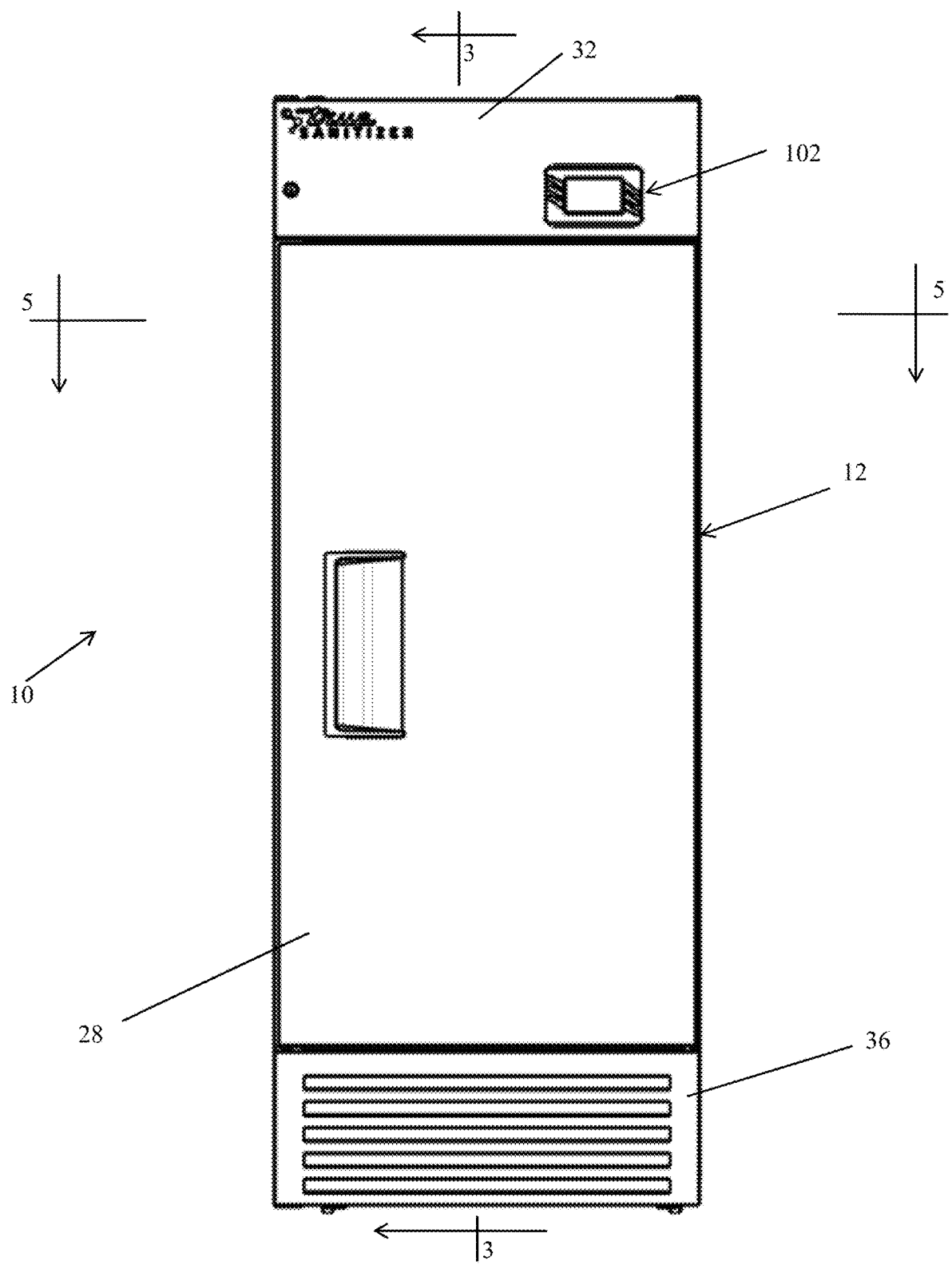
FIG. 2 is a front elevation of the sanitizing cabinet system.

The inventors have recognized that existing on-site sanitizing devices are not satisfactory for quickly sanitizing large volumes of articles. That is, existing sanitizing systems suffer from low throughput. Hence, the inventors have developed a new, large-capacity sanitizing cabinet system 10 for killing surface-borne pathogens such as viruses and bacteria. The sanitizing cabinet system 10 is believed to be particularly well-suited to sanitizing (and deodorizing) articles such as garments, footwear, and personal protective equipment (PPE), like masks, surgical gowns, respirators, surgical hoods, face shields, gloves, and the like.

Referring to FIGS. 1-8, the sanitizing cabinet system 10 comprises a large-volume enclosure or cabinet 12 that is configured to receive articles requiring sanitization (not shown). In the illustrated embodiment, the cabinet 12 is essentially the cabinet of a full-size commercial refrigerator of the type sold by True Manufacturing, Inc. As will be explained in further detail below, the cabinet 12 defines a sanitizing compartment 14, and the sanitizing cabinet system 10 further comprises ozone distribution passaging 16 in open fluid communication with the sanitizing compartment. An ozone generator 18 (broadly, a sanitizing fluid generator) is received in the ozone distribution passaging. A sanitizing air mover 20 is likewise received in the ozone distribution passaging for moving air from the sanitizing compartment 14 across the ozone generator 18 to form ozonated air (broadly, sanitizing fluid) and to move the ozonated air into the sanitizing compartment. The illustrated sanitizing cabinet system 10 further comprises an ozone conversion device 22 configured to be selectively opened to fluid communication with the sanitizing compartment 14 and closed from fluid communication with the sanitizing compartment. As explained below, the ozone conversion device 22 is configured to neutralize ozone in the sanitizing compartment when opened.

The cabinet 12 includes a back wall 24 and a pair of opposite side walls 26. A door 28 is mounted on the cabinet 12 opposite the back wall 24 and generally in front of the sanitizing compartment 14. The cabinet 12 includes an upper portion 30 above the sanitizing compartment 14 (broadly, a first portion adjacent to the sanitizing compartment). An upper access panel 32 is connected to the cabinet 12 generally in front of the upper portion 30 and generally above the door 28. The cabinet 12 also includes a lower portion 34 below the sanitizing compartment (broadly, a second portion adjacent to the sanitizing compartment and spaced apart from the first portion). A lower access panel 36 is connected to the cabinet 12 generally in front of the lower portion 34 and generally below the door. In the illustrated embodiment, part of the ozone distribution passaging 16, the sanitizing fan 20, and the ozone generator 18 are located in the upper portion 24 of the cabinet 12, and the ozone conversion device 22 is located in the lower portion 26 of the cabinet. It is contemplated that in other embodiments the locations of the components can be reversed, with ozone generator and sanitizing fan located in a lower cabinet portion generally below the sanitizing compartment and the ozone conversion device located in the upper cabinet portion generally above the sanitizing compartment. Still further, it is contemplated that the cabinet portions in which these components are received can have other adjacent positions with respect to the sanitizing compartment besides generally above and generally below (e.g., a first portion of the cabinet in which an ozone generator and/or sanitizing fan is received might be to one side of the sanitizing compartment and a second portion of the cabinet in which the ozone conversion device is received might be to another side or a spaced apart location along the same side of the sanitizing compartment). The upper access panel 32 is hinged and the lower access panel 36 is removable to allow access to the respective components in the upper and lower portions 30, 34.

In the illustrated embodiment, a bottom wall 38 of the sanitizing compartment 16 forms a dividing wall that separates the sanitizing compartment from the lower portion 34 (broadly, ozone conversion portion) of the cabinet 12. In the illustrated embodiment, the ozone conversion device 22 is attached to the dividing wall 38 and received in the lower portion 34. The dividing wall 38 comprises an inlet opening 40 and an outlet opening 42 spaced apart from the inlet opening. The inlet opening 40 and the outlet opening 42 provide fluid communication between sanitizing compartment 14 and the lower portion 34 of the cabinet. More particularly, the inlet opening 40 and the outlet opening 42 provide fluid communication between the ozone conversion device 22 and the sanitizing compartment 14 that enables the ozone conversion device 22 to neutralize ozone from the ozonated air inside the sanitizing compartment.

In an exemplary embodiment, the interior storage volume of the sanitizing compartment 14 is greater than 7 cubic feet. The volume of the illustrated sanitizing compartment 14 is approximately 9 cubic feet, e.g., the sanitizing compartment 14 has an internal height, width, and front-to-back depth of greater than 36 inches, 18 inches, and 15 inches, respectively. For purposes of measuring the internal dimensions of the sanitizing compartments, space inside the cabinet 12 occupied by the ozone distribution passing 16 is excluded. It is contemplated that cabinets of the other sizes may be used in one or more embodiments. For example, it is expressly contemplated that, instead of the full-height refrigerator cabinet format of the sanitizing cabinet system 10, the sanitizing cabinet system can utilize an under-counter refrigerator cabinet as the cabinet shell, or other cabinet-type enclosure of suitable size. The exterior of the illustrated cabinet 12 can be formed by stainless steel panels and the interior of the cabinet can be formed by aluminum panels. It is also contemplated that other materials can be used without departing from the scope of this disclosure. But internal materials should be able to withstand the presence of elevated levels of ozone.

In an exemplary embodiment, the sanitizing compartment 14 includes integrated shelf supports (not shown). Suitably, wire shelving (broadly, porous shelving; not shown) may be mounted on the shelf supports at vertically spaced locations along the height of the sanitizing compartment. In an embodiment, the shelves are arranged to each support a single layer of a certain type of articles thereupon such that all of the articles in the sanitizing compartment are spaced apart by a sufficient distance to allow substantial air flow along all surfaces of all articles. To ensure proper article spacing, it is contemplated that the shelves may including markings or divider structures that encourage users to position the articles at the desired spacing. In certain embodiments, the sanitizing compartment is equipped with hanging hooks or bars for suspending articles, such as garments, to be sanitized. The hanging hooks or bars may be used in lieu of or in addition to the porous shelving.

The door 28 is configured for opening and closing the sanitizing compartment 14. In other words, the door 28 is movable relative to the cabinet 12 between an open position and a closed position for selectively opening and closing the sanitizing compartment 14. Suitably, the door 28, when open, allows access to the sanitizing compartment 14. When the door 28 is closed, in one or more embodiments, it substantially seals the doorway or opening to the cabinet 12 so that the sanitizing environment inside the cabinet does to leak out through the interface between the door and the cabinet. For example, in the illustrated embodiment, the door 28 includes a gasket that extends around a perimeter margin of the door for sealing engagement with a front frame of the cabinet 12 when the door is closed. At least the upper access panel 32 (and in some embodiments, the lower access panel 36 also) likewise seal to the cabinet to prevent fluid leakage.

In the illustrated embodiment, the sanitizing cabinet system 10 further comprises an automatic door lock 44 (FIG. 5) configured for selectively locking and unlocking the door in the closed position. As will be explained in further detail below, the sanitizing cabinet system 10 uses the door lock 44 to ensure that unpermitted levels of ozone do not escape the cabinet 12 to the ambient environment.

Figure 3:
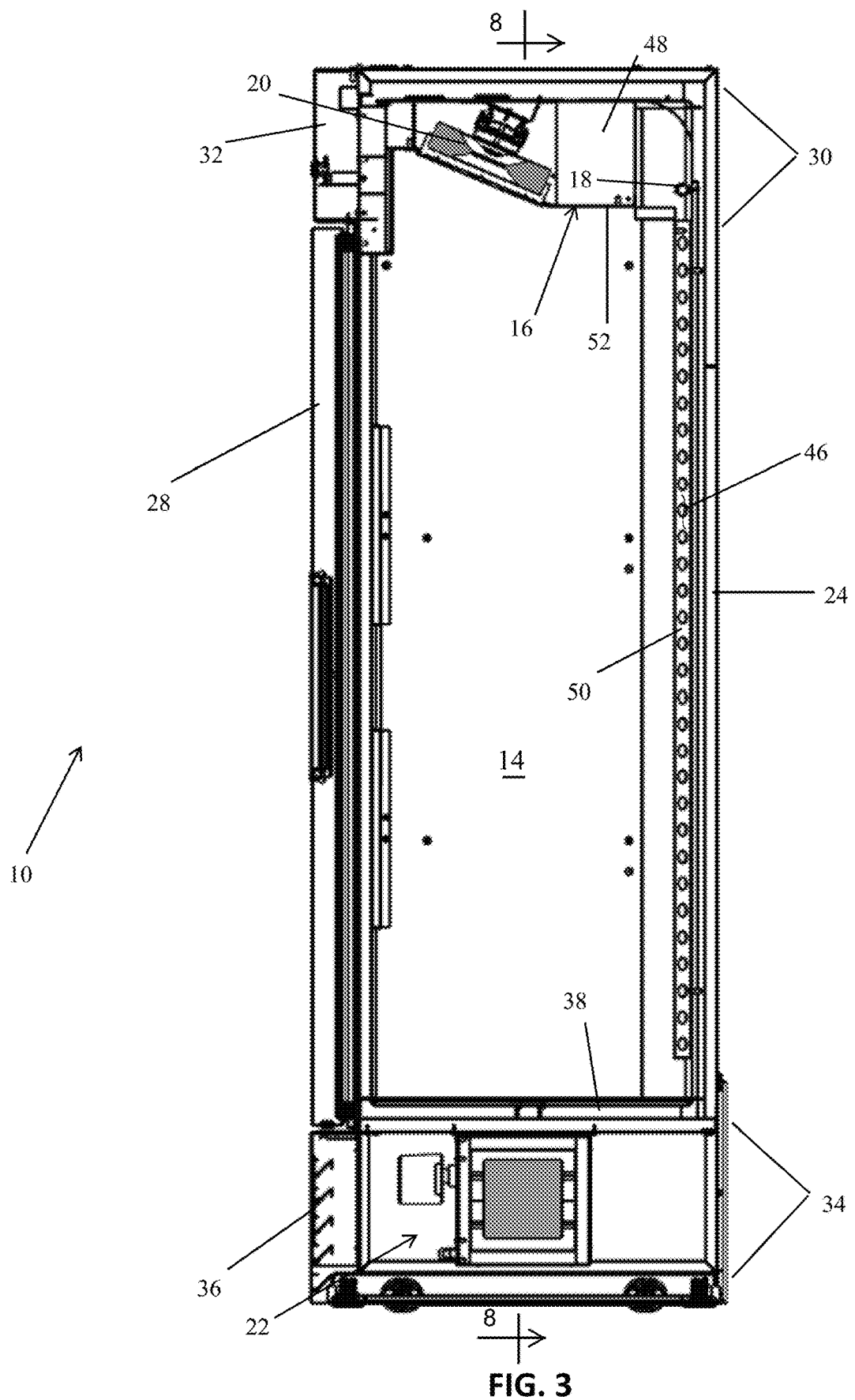
FIG. 3 is a cross section taken through the plane of line 3-3 of FIG. 2.
Figure 4:
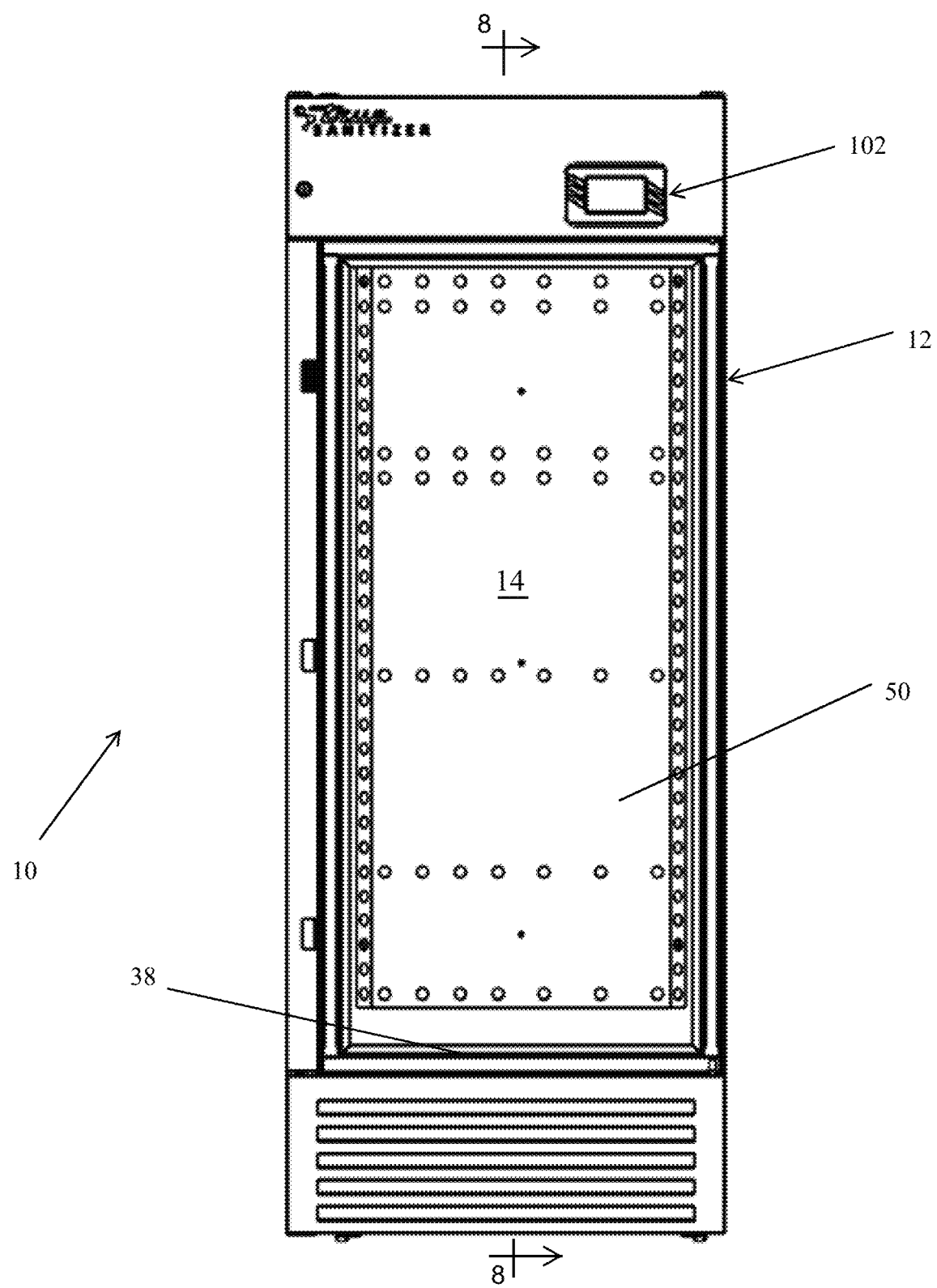
FIG. 4 is a front elevation of the sanitizing cabinet system with a door thereof removed.
Figure 5:
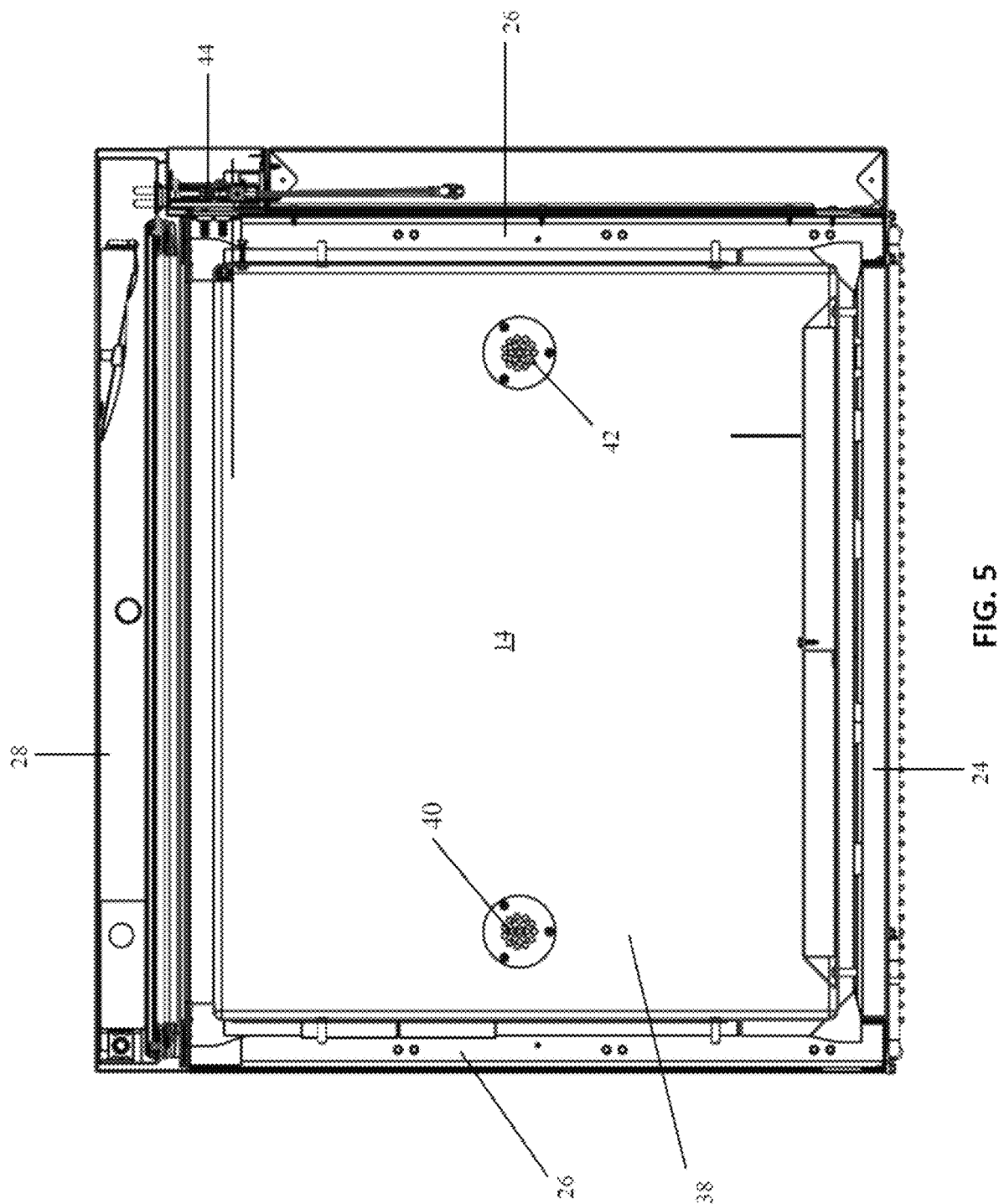
FIG. 5 is a cross section taken through the plane of line 5-5 of FIG. 2.
Figure 6:
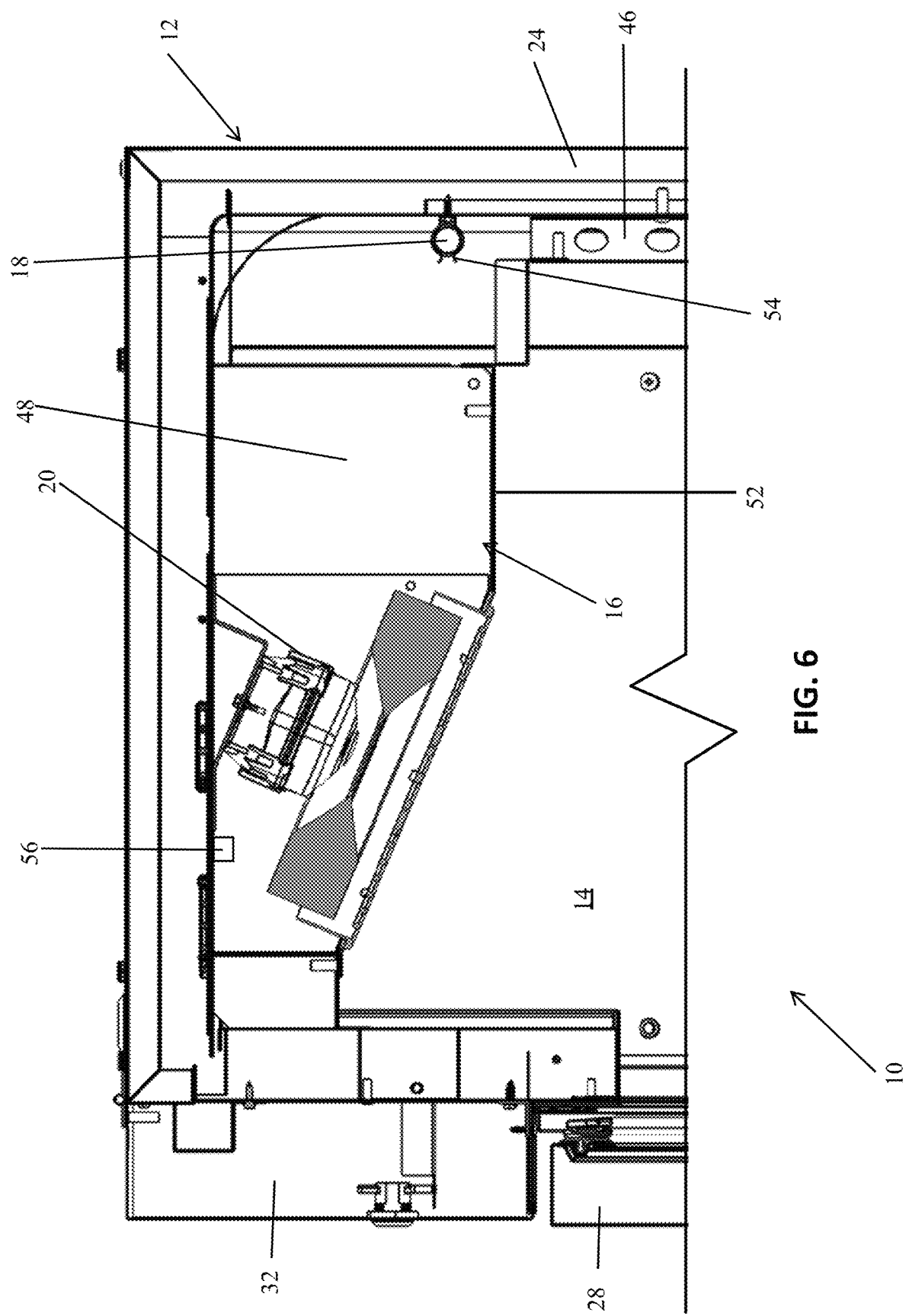
FIG. 6 is an enlarged fragmentary view of a portion of FIG. 3.
Figure 7:
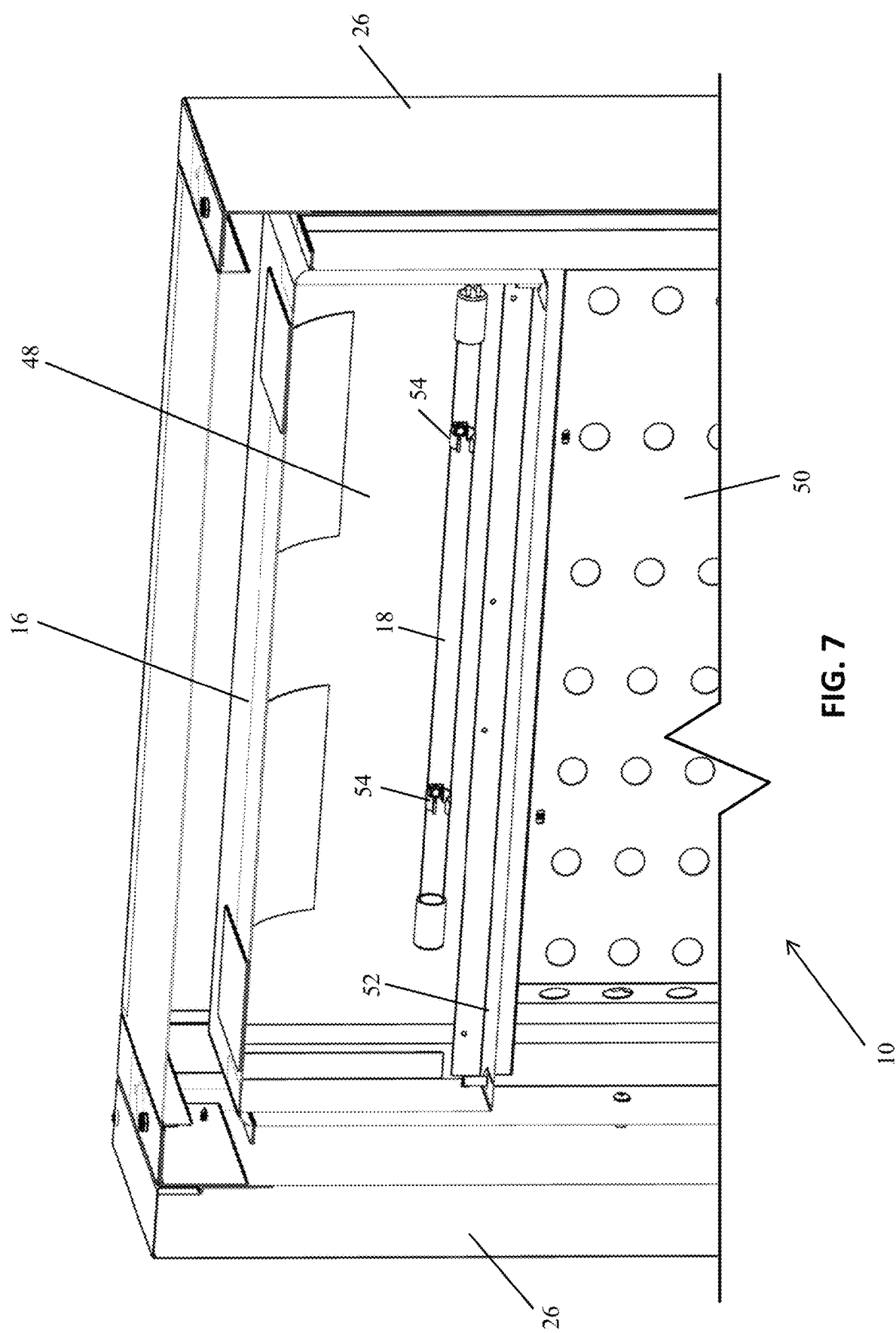
FIG. 7 is a fragmentary cross sectional perspective of the sanitizing cabinet system showing how an ozone generator is positioned within ozone distribution passaging of the sanitizing cabinet system.
Figure 8:
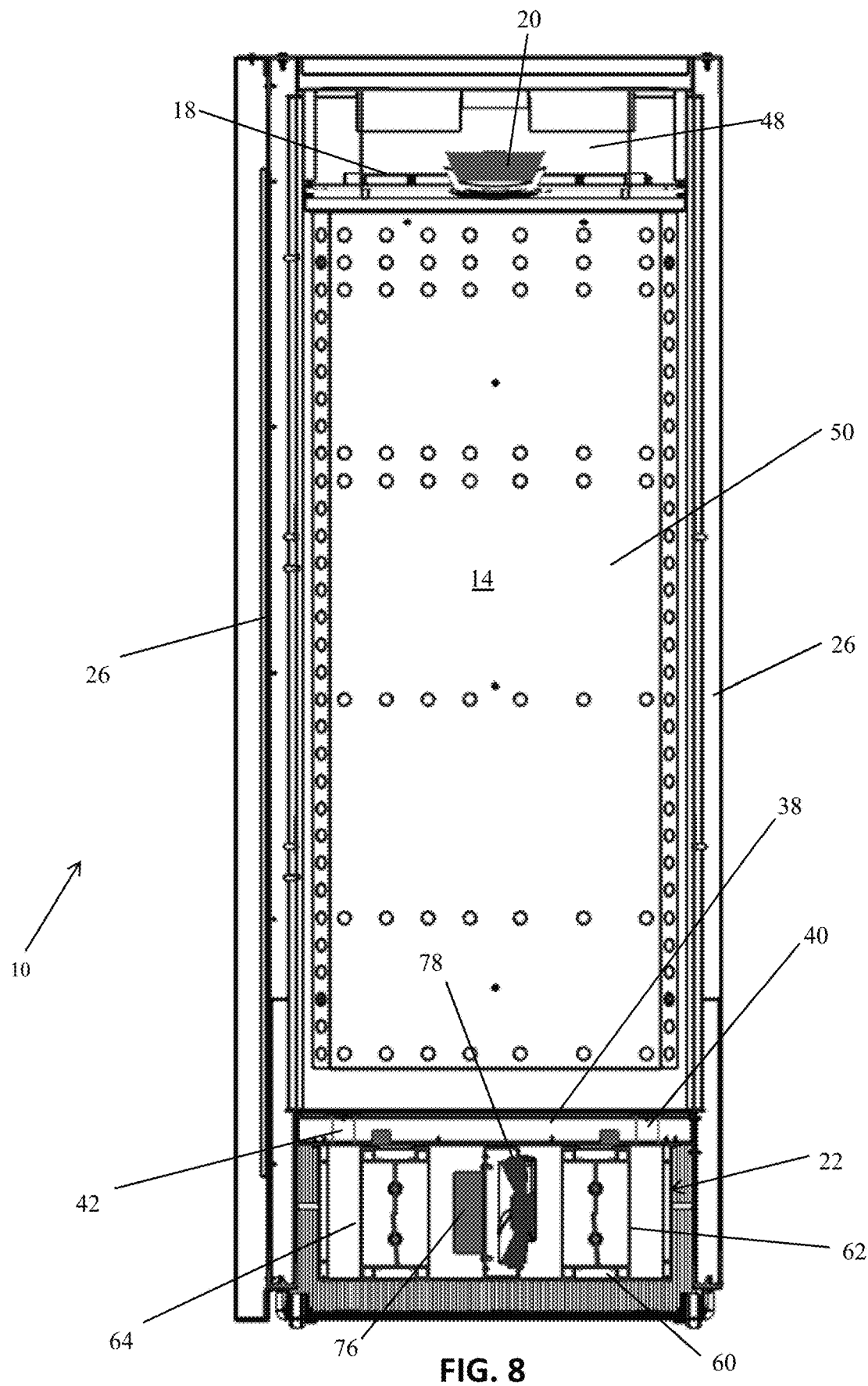
FIG. 8 is a cross-section taken through the plane of line 8-8 of FIG. 3.

Referring to FIGS. 3, 6, and 7, the ozone distribution passaging 16 comprises an ozone discharge plenum 46 and a blower plenum 48 (broadly, an air mover plenum). In one or more embodiments, the ozone discharge plenum 16 extends heightwise along the back wall 24 from an open upper end portion (which opens to the upper portion 30 of the cabinet) to an enclosed lower end portion, spaced apart above the dividing wall 38. The ozone discharge plenum 46 includes a front plenum wall 50 defining a plurality of orifices through which ozonated air can flow forward into the sanitizing compartment 14. In this case, the front plenum wall 50 defines part of the back of the sanitizing compartment 14. The front plenum wall 50 includes outlet openings at a plurality of vertically spaced apart location so that ozonated air is directed to flow across the articles supported on every shelf in the sanitizing compartment 14 (see FIG. 4).

In one or more embodiments, the blower plenum 48 is located directly below the top wall of the cabinet 12. In the illustrated embodiment, the blower plenum 48 is formed by the top wall of the cabinet and a lower plenum wall 52, which generally separates the blower plenum from the sanitizing compartment 14. The lower plenum wall 52 divides the upper portion 30 of the cabinet 12 from the sanitizing compartment 14 in the illustrated embodiment. The front end portion of the lower plenum wall 52 includes one or more return air inlet openings into which return air from the sanitizing compartment 14 can be drawn into the ozone distribution passaging 16. In the illustrated embodiment, the sanitizing fan 20 is received in the blower plenum 48 for drawing air into the blower plenum through the return air inlet openings. The fan 20 is further configured to blow air into the top end portion of the ozone discharge plenum 46 so that the air then travels downward along the ozone discharge plenum and is discharged through the ozone outlets at multiple points along the height of the cabinet 12 toward the articles received in the sanitizing compartment 14.

The ozone distribution passaging comprises a region connecting the blower plenum 48 and the ozone discharge plenum 46. The illustrated ozone generator 18 is located in this region, spaced apart rearwardly of the sanitizing fan 20. As can be seen the ozone distribution passaging 16 of the cabinet 12 is configured to enable the sanitizing fan 20 to direct ozonated air across the ozone generator 18, downward along the back wall, and then forward into the sanitizing compartment 14. Return air from the sanitizing compartment 14 is drawn upward into the blower plenum 48 generally at the front of the cabinet 12 and then is directed to flow backward toward the ozone generator 18 and the ozone distribution plenum 46.

Suitably, the sanitizing fan 20 is a relatively high-powered unit that generates a volumetric flow rate in an inclusive range of from about 200 $ft^3$/min to about 500 $ft^3$/min and/or a flow velocity of from about 4.5 ft/sec to about 10.5 ft/sec. Suitably the fan 20 creates turbulent air flow conditions throughout substantially the entire sanitizing compartment 14 of the cabinet 12 when the door 28 is closed. This enables the fan 20 to distribute the ozonated air along substantially the entire exposed surface area of each of the articles received in the cabinet 12.

In the illustrated embodiment, the primary mode of sanitization provided by the sanitizing cabinet system 10 is ozone or photoplasma sanitization (broadly, application of a sanitizing gas or fluid).

Figure 9:
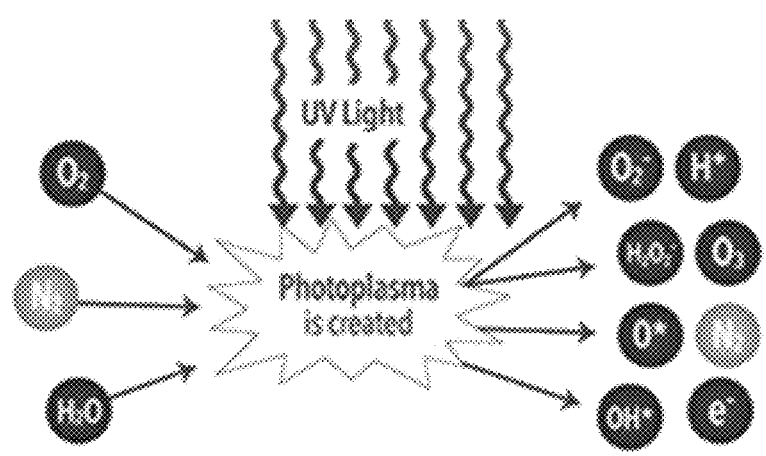
FIG. 9 is a schematic illustration of an ozone generation process.
Figure 10:
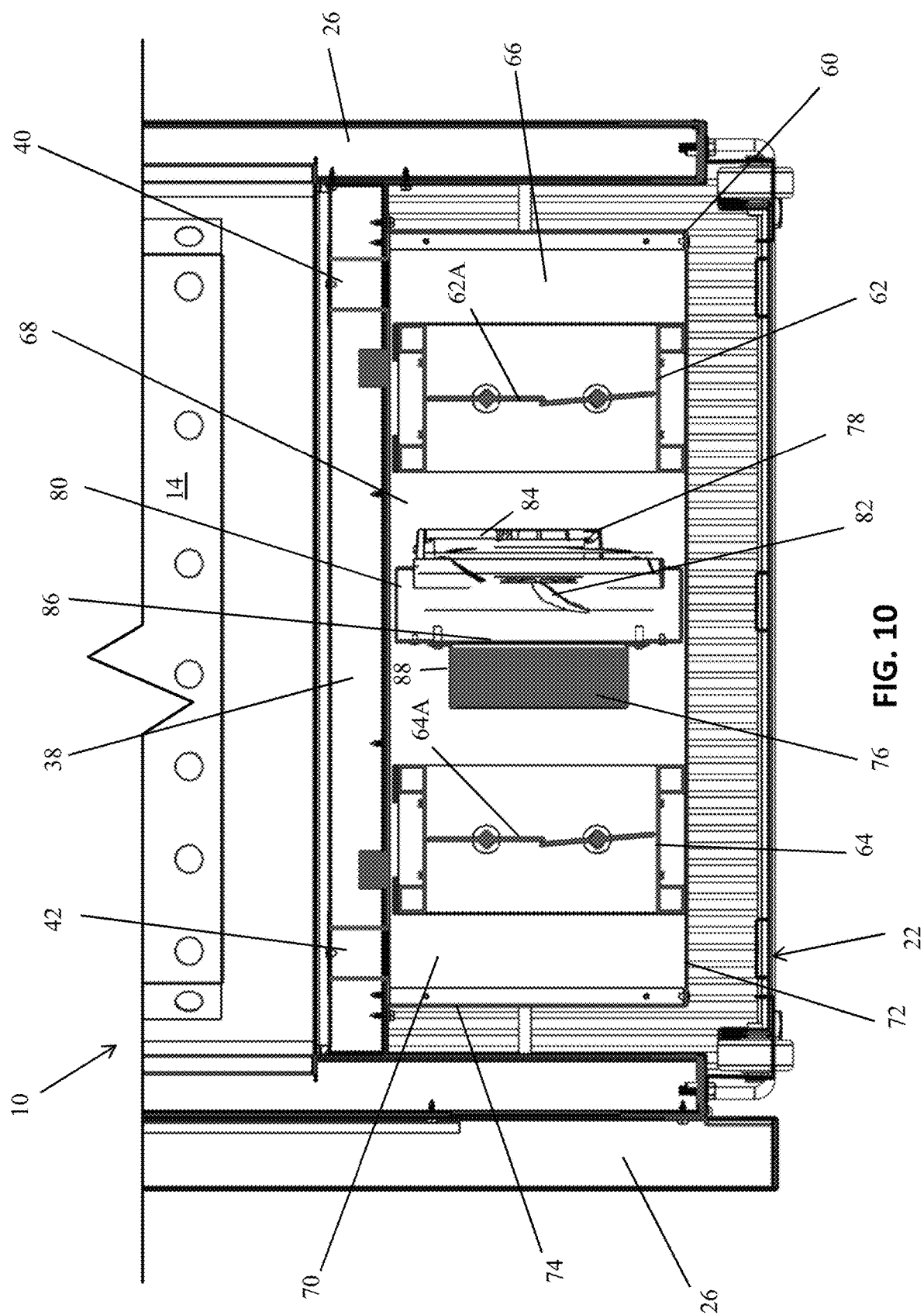
FIG. 10 is an enlarged fragmentary view of a portion of FIG. 8.
Figure 11:
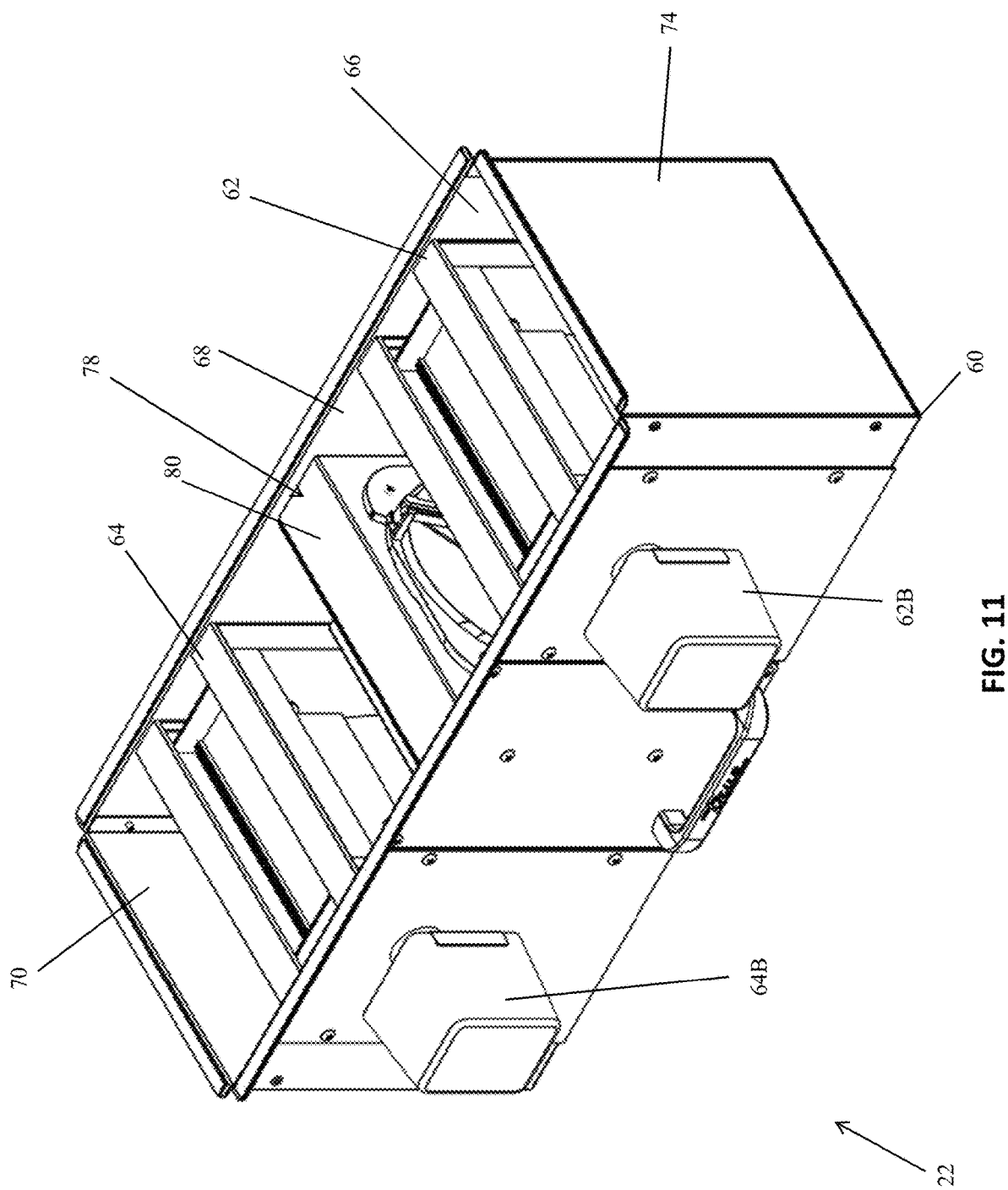
FIG. 11 is a perspective of an ozone conversion device of the sanitizing cabinet system.
Figure 12:
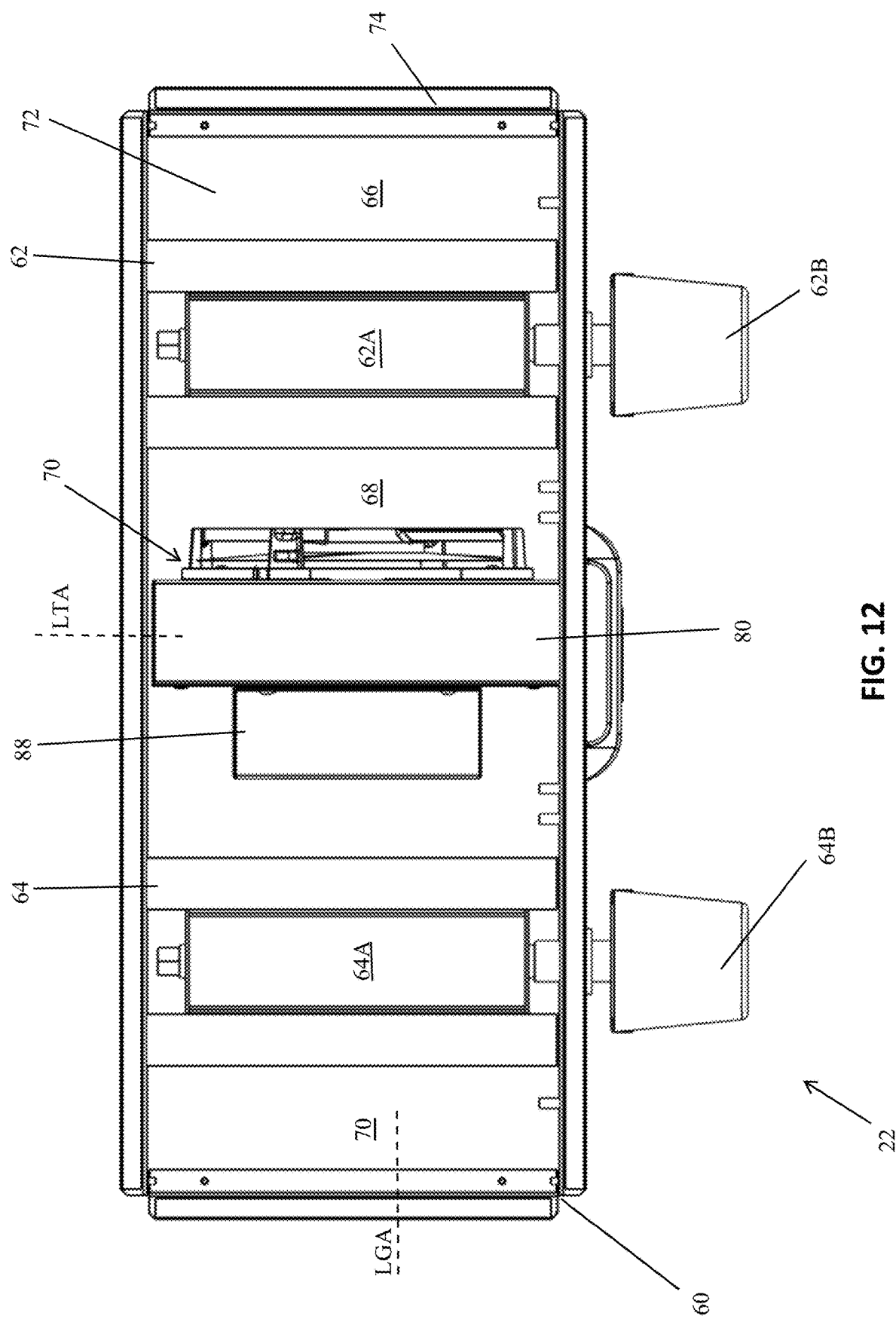
FIG. 12 is a top plan view of the ozone conversion device.
Figure 13:
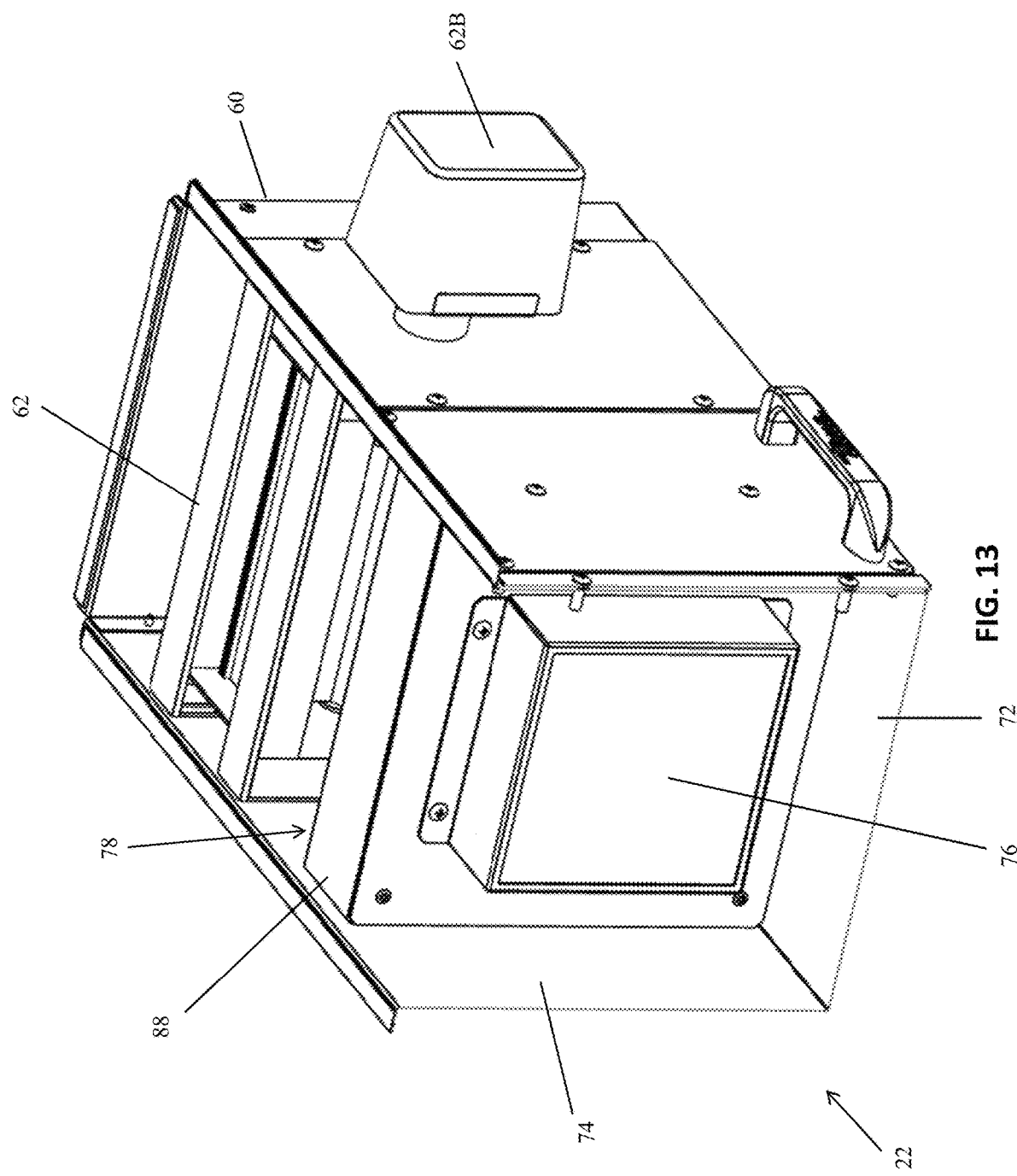
FIG. 13 is cross-sectional perspective of the ozone conversion device.

In an exemplary embodiment, the generator 18 is a photplasma generator of the type sold by Biozone Scientific of Orlando, Florida. Photplasma is thought to effectively reduce bactieria, viruses, mold, volatile organic compounds, and/or odors. Referring to FIG. 9, in principle, the photoplasma generator 18 operates by imparting high-energy ultraviolet (UV) light (i.e., electromagnetic radiation in the ultraviolet wavelength spectrum). Thus, in one or more embodiments, the ozone generator 18 comprises a UV light configured to energize components of the air inside the cabinet 12 to form high-energy plasma (ozonated air). For example, the UV light forms charged molecules, ozone, and free electrons. The resulting fluid stream has the capacity to kill most pathogens found on the surfaces of articles, including, it is believed, the capacity to kill the coronavirus, COVID-19.

In an exemplary embodiment, the ozone generator 18 comprises one or more low-pressure mercury discharge tubes configured to generate UV light at two wavelengths of interest: a first wavelength in an inclusive range of from 175 nm to 195 nm (e.g., a wavelength of about 185 nm) and a second wavelength in an inclusive range of from 240 nm to 265 nm (e.g., a wavelength of about 254 nm). The UV light at the first wavelength is configured to decompose oxygen molecules and synthesize ozone. The UV light at the second wavelength is configured to decompose ozone and produce high energy activated oxygen.

In one or more embodiments, the ozone generator 18 has a 'low-ozone configuration. In this disclosure, a generator 20 with a low-ozone configuration is configured to generate a fluid containing less than 0.1 ppm ozone, to ensure compliance with regulations promulgated by the Occupational Safety and Health Administration (OSHA) for regular indoor use of the sanitizing cabinet system 10, or a fluid containing less than 0.05 ppm to ensure compliance with regulations promulgated by the Food and Drug Administration (FDA) for situations in which the sanitizing cabinet system is used for medical devices and thus falls under the purview of FDA. When the ozone generator has a low-ozone configuration, the sanitizing cabinet system can be operated without safety interlocks or the automatic door lock 44. Thus, a sanitizing cabinet system 10 comprising a generator 18 having a low-ozone configuration may include a simplified control system, which enables the sanitizing cabinet system to be produced at scale quickly and relatively inexpensively. For example, in certain embodiments, refrigerator manufacturers and/or manufacturers of other types of large cabinet devices can adapt existing cabinet inventory for use as sanitizing cabinets very quickly during a pathogenic emergency, such as an epidemic or pandemic. This can help meet rapidly the increasing demand for frequent sanitization of various types of articles and equipment during a pathogenic emergency.

In certain embodiments, the generator 18 is configured to generate ozonated air inside the cabinet 12 containing a greater amount of ozone—e.g., greater than 0.1 ppm ozone, greater than 0.5 ppm ozone, greater than 0.8 ppm ozone, greater than 1.5 ppm ozone, greater than 2.0 ppm ozone, greater than 2.5 ppm ozone, or greater than 3.0 ppm ozone. A generator 18 with this type of high-ozone configuration enables the sanitizing cabinet system 10 to execute much shorter sanitizing cycles to achieve the same sanitization effect. However, since emission of ozone in excess of 0.05 ppm is not permitted by the FDA and emission of ozone in excess of 0.1 ppm is not permitted by OSHA, when this type of high-ozone generator 18 is used, the sanitizing cabinet system 10 preferably includes a safety system for preventing excessive levels of ozone from being emitted directly to the external environment (discussed below).

In the illustrated embodiment of the sanitizing cabinet system 10, the ozone generator 18 is placed directly into the ozone distribution passaging 16 for generating ozone inside the cabinet 12. More particularly, the illustrated ozone generator 18 comprises an unenclosed high powered UV bulb of generally the type described above, along with a corresponding power supply and fixture. The bulb 18 is suitably located in the ozone distribution passaging 16 downstream of the sanitizing fan 20 so that air blown by the fan passes over the bulb before being discharged through the ozone discharge plenum 46 (see FIGS. 6 and 7). As explained above, the bulb 18 is located generally at the region of the ozone distribution passaging where the blower plenum 48 connects to the ozone discharge plenum 46 (e.g., adjacent the upper end portion of the ozone discharge plenum and adjacent the rear end portion of the blower plenum). In the illustrated embodiment, the bulb 18 comprises a single, straight tube releasably mounted on the cabinet 12 via U-shaped clamps 54 that are screwed into the back wall 24. As will be explained in further detail below, the bulb 18 is a replaceable or expendable part, and the releasable mount provided by the clamps 54 enables quick replacement of the bulb when needed.

Suitably, the ozone generating bulb 18 is sized and arranged in relation to the ozone distribution passaging 16 to affect a substantial portion of the air that the fan 20 blows across the bulb. In one or more embodiments, the ozone generating bulb 18 comprises a tube having a length and a diameter. Suitably, the bulb 18 is mounted on the cabinet 212 so that the length of the bulb extends in the widthwise direction of the cabinet. The upper end portion of the ozone discharge plenum 46 has a width along the width of the cabinet 12. In certain embodiments, the bulb 18 is mounted in the cabinet so that the length of the bulb extends at least 75% of the width of the upper end portion of the ozone discharge plenum 46 (e.g., at least 80%, at least 85%, at least 90%, at least 95%). The upper end portion of the ozone discharge plenum 46 also has a front-to-back depth. In one or more embodiments, the diameter of the bulb 240 is at least 10% of the front-to-back depth of the upper end portion of the ozone discharge plenum (e.g., at least about 15%, at least about 20%, at least about 25%).

In summary, the sanitizing cabinet system 10 comprises an ozone generating light bulb 18 situated inside the cabinet 12 in open air fluid communication with a sanitizing compartment 14. In this disclosure, 'open' fluid communication means fluid communication that cannot be closed off by any valve, damper, or other manufactured closure component of the sanitizing cabinet system 10. Further the sanitizing cabinet system 10 comprises plenum walls 50, 52 that define ozone distribution passaging 16 inside the cabinet 12, and in which the ozone generating bulb 18 is received. The sanitizing cabinet system 10 still further comprises a fan 20 that is configured to draw air from the sanitizing compartment 14 into ozone distribution passaging 16 through a return air inlet at the upper front portion of the sanitizing compartment. The fan 20 is configured to move the return air forward through a blower plenum 48 and then across the ozone generating bulb 18 so that a substantial portion of the air is affected by the bulb. This generates ozone and forms ozonoted air. The fan 20 moves the ozonated air downward through the ozone discharge plenum 46 and causes the ozonated air to be discharged forward through the outlets in the front plenum wall 50 at a plurality of spaced apart locations along the height of the sanitizing compartment 14. Accordingly, it can be seen that the sanitizing cabinet system 10 is configured to direct ozonated air along substantially the full height of the sanitizing compartment 14 to sanitize articles placed at any location within the sanitizing compartment.

Although not depicted in the drawings above, it is expressly contemplated that the sanitizing cabinet system 10 may incorporate one or more secondary sanitizing systems in addition to the primary ozone/photoplasma generator 18. For example, in one or more embodiments, the system 10 includes a plurality of sanitizing UV lights (not shown) in the sanitizing compartment 14 that are configured to sanitize articles contained therein by direct application of UV light.

In an exemplary embodiment, the sanitizing cabinet system further comprises an ozone sensor 56 (broadly, a gas detection sensor) configured to output a signal representative of the amount (e.g., concentration) of ozone inside the cabinet 12. In the illustrated embodiment, the ozone sensor 56 is located in the ozone distribution passaging. More particularly, the ozone sensor 56 is located in the blower plenum 48, adjacent to the sanitizing fan 20. Any suitable gas sensor capable outputting a signal representative of ozone concentration in the sanitizing compartment 14 may be used without departing from the scope of the disclosure. In one or more embodiments, the ozone sensor 56 comprises a SPEC Sensor™ electrochemical gas sensor.

Referring to FIGS. 10-13, the illustrated ozone conversion device 22 comprises a housing 60 defining an interior space and first and second dampers 62, 64 received in the housing in the interior space for dividing the interior space of the housing between an upstream chamber 66, an ozone conversion chamber 68, and a downstream chamber 70.

The illustrated housing 60 forms a generally rectangular enclosure with an open side (e.g., an open top side). The housing 60 has a base portion 72 and a perimeter portion 74 extending from the base portion to a free edge margin. The perimeter portion 74 comprises a first end wall and a second end wall spaced apart along a longitudinal axis LGA and a first side wall and a second side wall spaced apart along a lateral axis LTA. The free edge margin of the perimeter wall 74 circumscribes an open side of the housing opposite the base portion 72. In other words, the illustrated housing 60 comprises an opening to the interior of the housing that extends longitudinally from the first end wall to the second end wall and laterally from the first side wall to the second side wall.

The first and second dampers 62, 64, are spaced apart along the longitudinal axis LGA between the first end wall and the second end wall of the housing perimeter portion 74. Each damper 62, 64 comprises an assembly that extends laterally from the first side wall of the perimeter portion 74 to the second side wall. Each damper 62, 64 also extends vertically from the base portion 72 to an upper end portion adjacent the free edge margin of the perimeter portion 74 of the housing 60. Thus, in the illustrated embodiment, the dampers define chambers 66, 68, 70 that are spaced apart along the longitudinal axis LGA of the housing 60.

The first and second dampers 62, 64 are configured to be selectively opened and closed. Each damper 62, 64 comprises a respective damper plate assembly 62A, 64A including one or more rotatable damper plates and a respective damper actuator 62B, 64B (e.g., electric motor or solenoid) configured to selectively rotate the plates of the damper plate assembly between an open position (not shown) and the closed position shown in the drawings. When the first and second dampers 62, 64 are closed, they fluidly separate the ozone conversion chamber 68 from the upstream chamber 66 and the downstream chamber 70; and when the dampers are open, they provide fluid communication between the three chambers.

In addition to the dampers 62, 64, the illustrated ozone conversion device housing 60 receives ozone conversion catalyst 76 and an ozone conversion air mover 78. Suitably, the ozone conversion catalyst 76 comprises ozone neutralizing catalyst material, such as a catalyst material made of an aluminum compound and/or a manganese compound that is configured to convert an ozone into dioxygen. In the illustrated embodiment, the ozone conversion catalyst 76 and the ozone conversion air mover 78 are each received in the ozone conversion chamber 68. It is conceivable, however, to place the ozone conversion air mover in one of the other chambers 66, 70 instead. The ozone air mover 78 comprises a fan enclosure 80 and a fan 82 in the fan enclosure. The fan enclosure 80 extends laterally from the first side wall of the perimeter portion 74 to the second side wall. The fan enclosure 80 also extends vertically from the base portion 72 to an upper end portion adjacent the free edge margin of the perimeter portion 74 of the housing. The fan enclosure 80 comprises an upstream end defining an inlet opening 84 and a downstream end defining an outlet opening 86. The upstream end and the downstream end are spaced apart along the longitudinal axis LGA. The fan 82 is configured to draw air into the fan enclosure 80 through the inlet opening 84 and discharge air out of the fan enclosure through the outlet opening 86. The ozone conversion catalyst 76 is supported on the downstream end of the fan enclosure 80 such that substantially all of the air discharged out of the fan enclosure through the outlet opening 86 must pass through the ozone conversion catalyst. For example, in the illustrated embodiment, the ozone conversion catalyst 76 is supported in a shroud 88 extending longitudinally from the downstream end of the fan enclosure 80 and extending circumferentially about the outlet opening 86.

The housing 60 is configured to mount on the dividing wall 38 of the sanitizing cabinet system 10 such that the upstream chamber 66 fluidly communicates with the inlet opening 40 formed in the dividing wall 38 and the downstream chamber 70 fluidly communicates with the outlet opening 42 formed in the dividing wall. In an exemplary embodiment, a seal or gasket is placed between the free edge margin of the perimeter portion 74 of the housing and the dividing wall 38, as well as between the dividing wall and the upper end portions of the first and second dampers 62, 64 and the fan enclosure 80, to form a fluid seal of the interface between the ozone conversion device 22 and the dividing wall 38. The fluid seal maintains fluid separation between the chambers 66, 68, 70 at the interface between the ozone conversion device 22 and the housing. Hence, when the first and second dampers 62, 64 are closed, they fluidly separate the ozone conversion chamber 68 and the catalyst 76 contained therein from the inlet and outlet openings 40, 42, and thereby fluidly isolate the catalyst from the sanitizing compartment 14. But when the dampers 62, 64 are open, they provide fluid communication between the inlet and outlet openings 40, 42 and the ozone conversion chamber 68 so that the ozone conversion fan 82 can draw ozonated air from the sanitizing compartment 14 through the inlet opening 40, from the inlet opening into the upstream chamber 66, from the upstream chamber across the first damper 62 into the ozone conversion chamber and through the inlet opening 84 of the fan enclosure, from the inlet opening through the outlet opening 86 and further through the catalyst 76 contained in the shroud. The catalyst 76 neutralizes ozone in the ozonated air as it flows through the catalyst. The fan 82 moves the air out of the catalyst 76 across the second damper 64, into the downstream chamber 70 and then through the outlet opening 42 back into the sanitizing compartment.

As discussed above, in certain embodiments, the generator 18 is configured to generate sanitizing fluid containing ozone in an amount less than ozone emission standards promulgated by the relevant regulatory body. This permits the sanitizing fluid generated by the generator 18 to be emitted directly to atmosphere. A simplified system of this type can be configured to continuously operate the generator 18. A user simply places articles in the sanitizing compartment 14 whenever sanitizing is required, and then leaves them to be sanitized by the sanitizing cabinet system 10 for the required amount of time.

Figure 14:
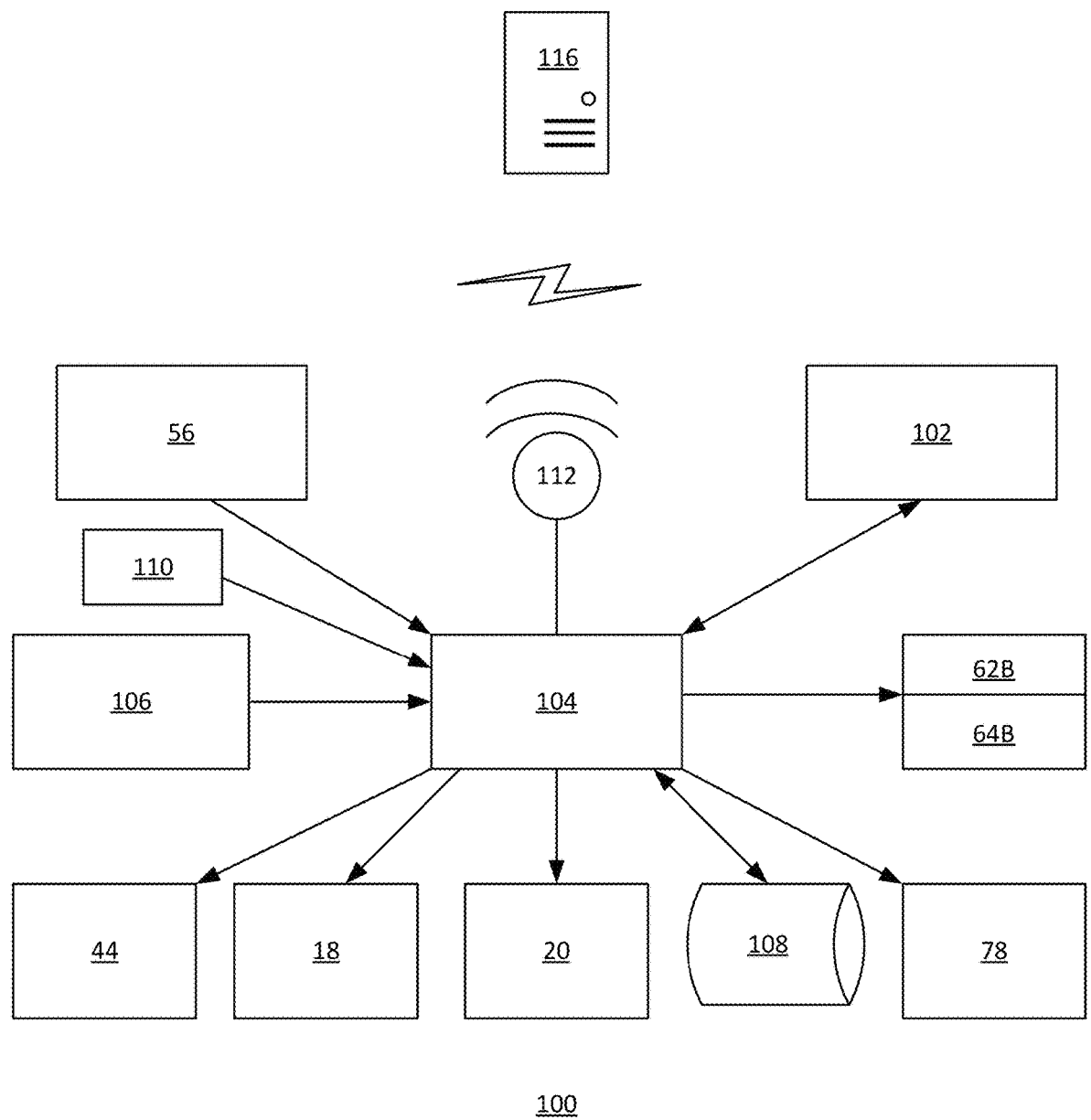
FIG. 14 is a schematic block diagram of a control system of the sanitizing cabinet system.
Figure 15:
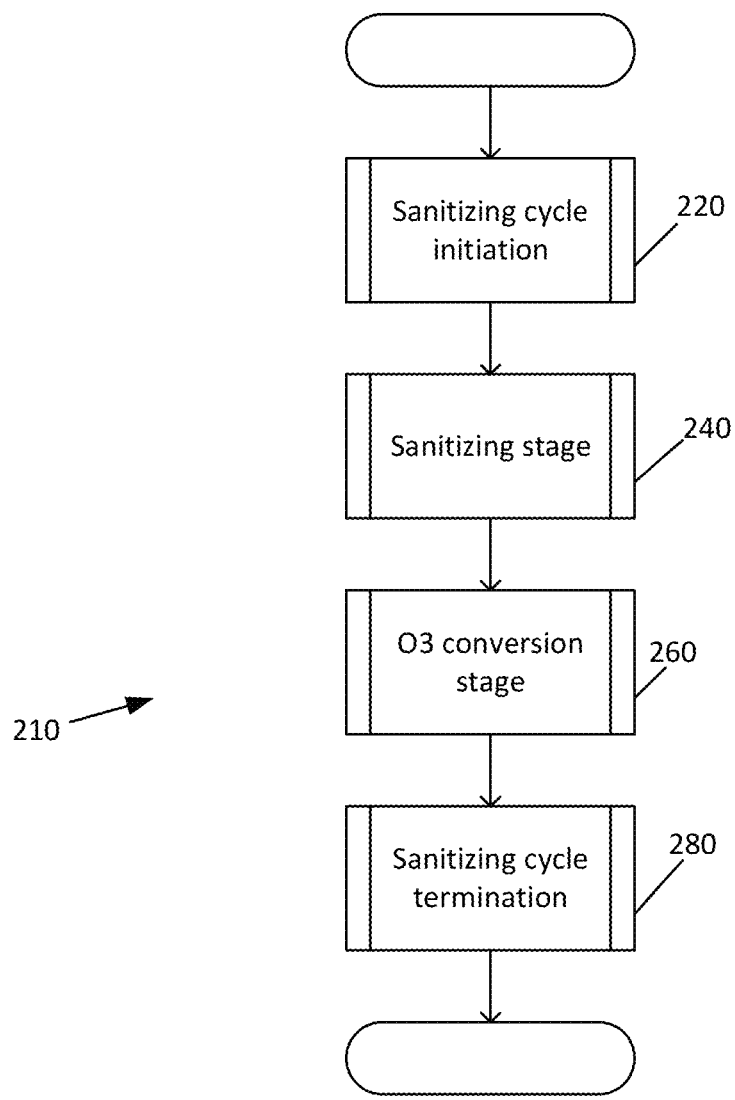
FIG. 15 is a flowchart of the subroutines of a process of sanitizing articles using the sanitizing cabinet system.
Figure 16:
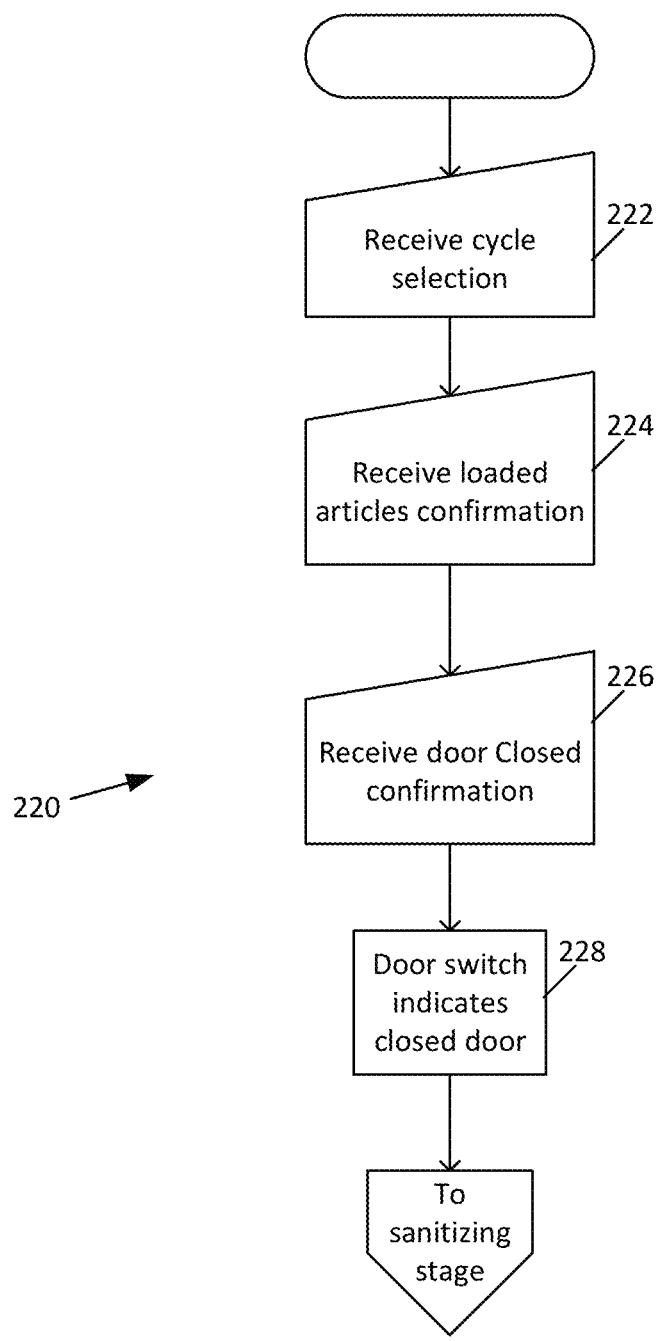
FIG. 16 is a flowchart of a sanitizing cycle initiation subroutine of the process of FIG. 15.

A generator 18 that generates greater amounts of ozone may be desired to reduce the sanitization cycle time. Referring to FIG. 14, in this case, the sanitizing cabinet system 10 may comprise an automated control system 100 that automatically directs sanitizing cycles and prevents the generator 18 from releasing excessive amounts of ozone to atmosphere. In the illustrated embodiment, the control system 100 comprises a user interface 102 (which in the illustrated embodiment comprises a touchscreen display mounted on the upper access panel 32 as shown in FIG. 1), a controller 104, the ozone sensor 56, the automatic door lock 44, a door switch 106 configured to detect when the door is closed, a memory 108 for storing historical information about the sanitizing cycles that have been performed by the cabinet system 10, and a temperature sensor 110 for detecting an internal temperature of the sanitizing compartment 14. The illustrated controller 104 is also operatively connected to the ozone generator 18, the sanitizing fan 20, the ozone conversion fan 78, and the damper actuators 62B, 64B for controlling these components. The illustrated controller 104 is further connected to an internet communication interface 112, for example, a wireless interface such as a cellular network or Wi-Fi transceiver. As shown in FIG. 14, the transceiver 112 enables the controller 104 to communicate over the internet with a remote server 116 (e.g., a remote monitoring server or a remote asset management server) to enable remote monitoring and/or control of the sanitizing cabinet system 10.

The controller 104 can include at least one processor for controlling the operation of the one or more output components based on one or more input components. The processor of the controller 104 may include a non-transitory processor-readable medium storing code representing instructions to cause the processor to perform a process. The processor may also access some or all of the code from the memory 108. The processor 104 may be, for example, a commercially available microprocessor, an application-specific integrated circuit (ASIC) or a combination of ASICs, which are designed to achieve one or more specific functions, or enable one or more specific devices or applications. In certain embodiments, the controller 104 may be an analog or digital circuit, or a combination of multiple circuits. The controller 104 may also include one or more memory components for storing data in a form retrievable by the controller. The controller 104 can store data in or retrieve data from the one or more memory components or the memory 108. Although a single schematic controller element is depicted in FIG. 14, it will be understood that various controls of the sanitizing cabinet system 10 can be implemented by different pieces of coordinated or independent control hardware. That is, while a single schematic element 104 is shown controlling numerous aspects of the system 10, it is to be understood that responsibility for controlling any of these aspects can be distributed among more than one control processor, circuit, or other control hardware.

During use, the controller 104 maintains the ozone generator 18, the sanitizing fan 20, and the ozone conversion device 22 in off state unless a sanitizing cycle is in process. In this off state, the automatic door lock 44 is unlocked so that a user can place articles in need of sanitizing into the sanitizing compartment 14 (e.g., on shelves, or suspended from hooks or hanging rods).

FIGS. 15-18 depict an exemplary process, generally indicated at 210, by which the controller 104 can conduct automated sanitizing cycles to sanitize articles at the direction of a user. The process 210 broadly includes a cycle initiation routine 220 in which the controller 104 receives user inputs to the user interface 102 that initiate a sanitizing cycle. Upon completion of the initiation routine 220, the controller 104 conducts the sanitizing cycle. Each sanitizing cycle comprise a sanitizing stage 240 and a conversion stage 260. As explained below, during each sanitizing stage 240, the controller 104 is configured to activate the ozone generator 18 and the sanitizing fan 20, deactivate the ozone conversion air mover 78, and close the first and second dampers 62, 64; and during each conversion stage 260, the controller 104 is configured to deactivate the ozone generator 18 and the sanitizing fan 20, activate the ozone conversion air mover 78, and open the first and second dampers 62, 64. And upon completion of the conversion stage 260, the controller 104 conducts a sanitizing cycle termination routine 280.

Figure 19:
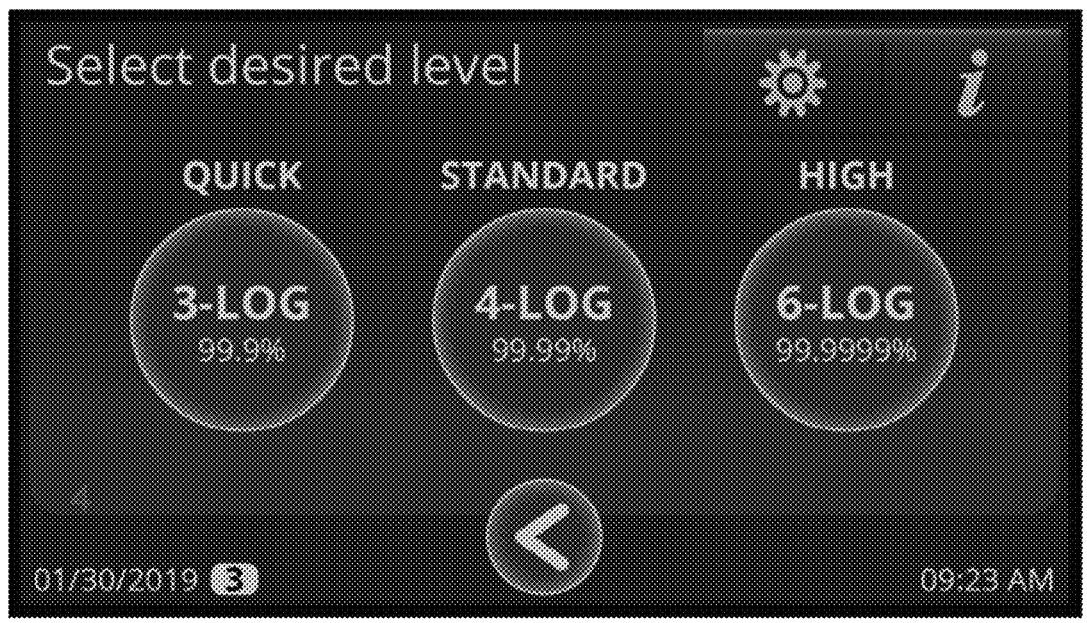
FIG. 19 is an exemplary screenshot of a sanitizing cycle selection view displayed on a user interface of the sanitizing cabinet system to enable user selection of a sanitizing cycle from among a plurality of sanitizing cycle options.
Figure 20:
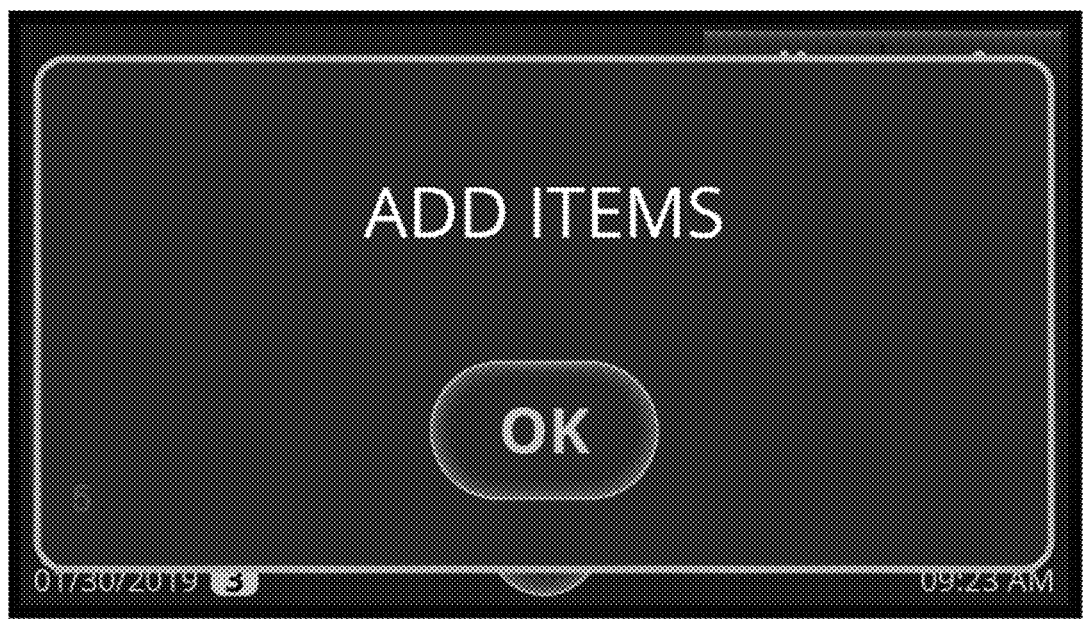
FIG. 20 is an exemplary screenshot of a pop-up displayed on the user interface to request user confirmation that items have been added to a sanitizing compartment of the sanitizing cabinet system during the initiation subroutine.
Figure 21:
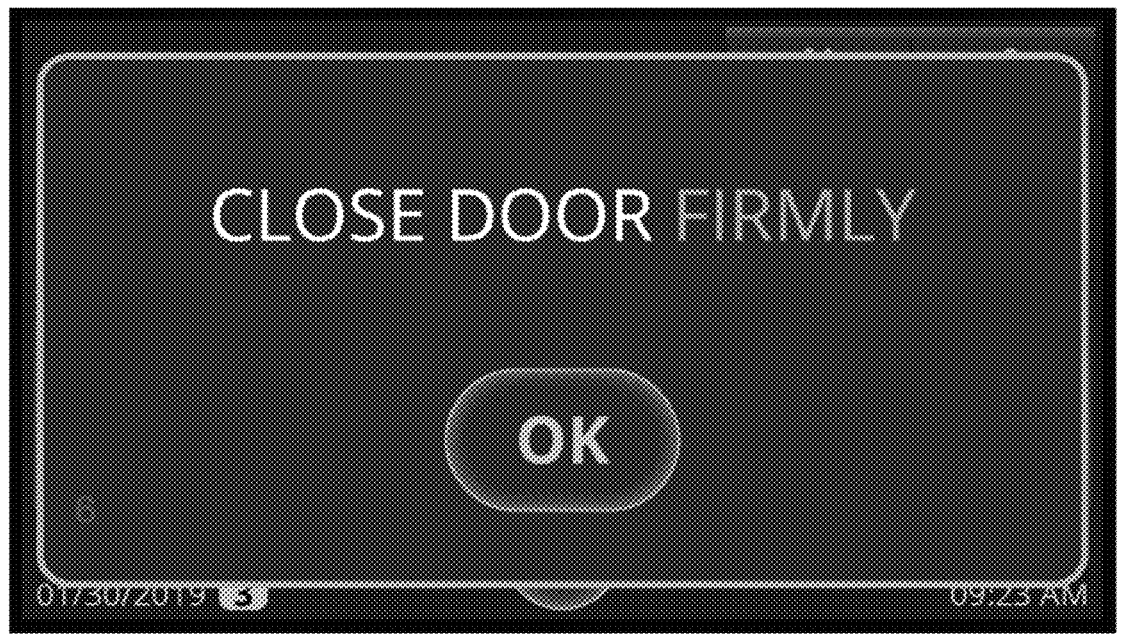
FIG. 21 is an exemplary screenshot of a pop-up displayed on the user interface to request user confirmation that the door is closed firmly during the initiation subroutine.

Referring to FIGS. 16 and 19-21, during the initiation routine 220, the controller 104 receives user inputs made to the user interface 102 selecting a sanitizing cycle (step 222), confirming that articles have been loaded into the sanitizing compartment 14 (step 224), and confirming that the door 28 of the cabinet has been closed (step 226). During this portion of the process, the user opens the door 28 to the cabinet 12, places articles in the sanitizing compartment 14, and shuts the door. An exemplary touchscreen display to facilitate user selection of a sanitizing cycle in step 222 is depicted in FIG. 19, and an exemplary touchscreen display to facilitate user confirmation of article placement (step 224) and door closure (step 226) are shown in FIGS. 20 and 21.

Accordingly, in the illustrated embodiment, the user interacts with the user interface device 102 to select a desired cycle type. The controller 104 is configured to selectively execute a plurality of (e.g., three) different sanitizing cycles (e.g., a quick cycle, a standard cycle, and a deep clean cycle; a 2-log reduction cycle, a 4-log reduction cycle, or a 6-log reduction cycle; or a 99.9% sanitization cycle, a 99.99% sanitization cycle, and a 99.9999% sanitization cycle) at the selection of the user via the user interface 102. In one or more embodiments, the memory 108 stores 'recipes' or formulas for sanitizing particular items in particular quantities. Instead of selecting from generic sanitizing cycles of different strengths as shown in FIG. 19, the user would select the type of items to be sanitized and the quantities and the controller would automatically execute a calibrated sanitizing cycle to perform based on the selection.

Referring again to FIG. 16, the controller 302 will not allow the sanitizing cycle to begin until the door switch 106 registers that the door 28 is in the closed position. The controller 104 is configured to maintain the ozone generator 18 in an off state unless the automatic door lock 44 locks the door 28 in the closed position. After receiving the door closed signal from the door switch 106 (step 228), the controller 104 can proceed to the sanitizing stage 240 of the sanitizing cycle. It is contemplated that the sanitizing cabinet system 110 can also include a redundant, hardwired interlock, independent of the controller 104, which prevents power from being supplied to the generator 18 unless the door 216 is closed and the lock 44 is in the locked position.

Figure 17:
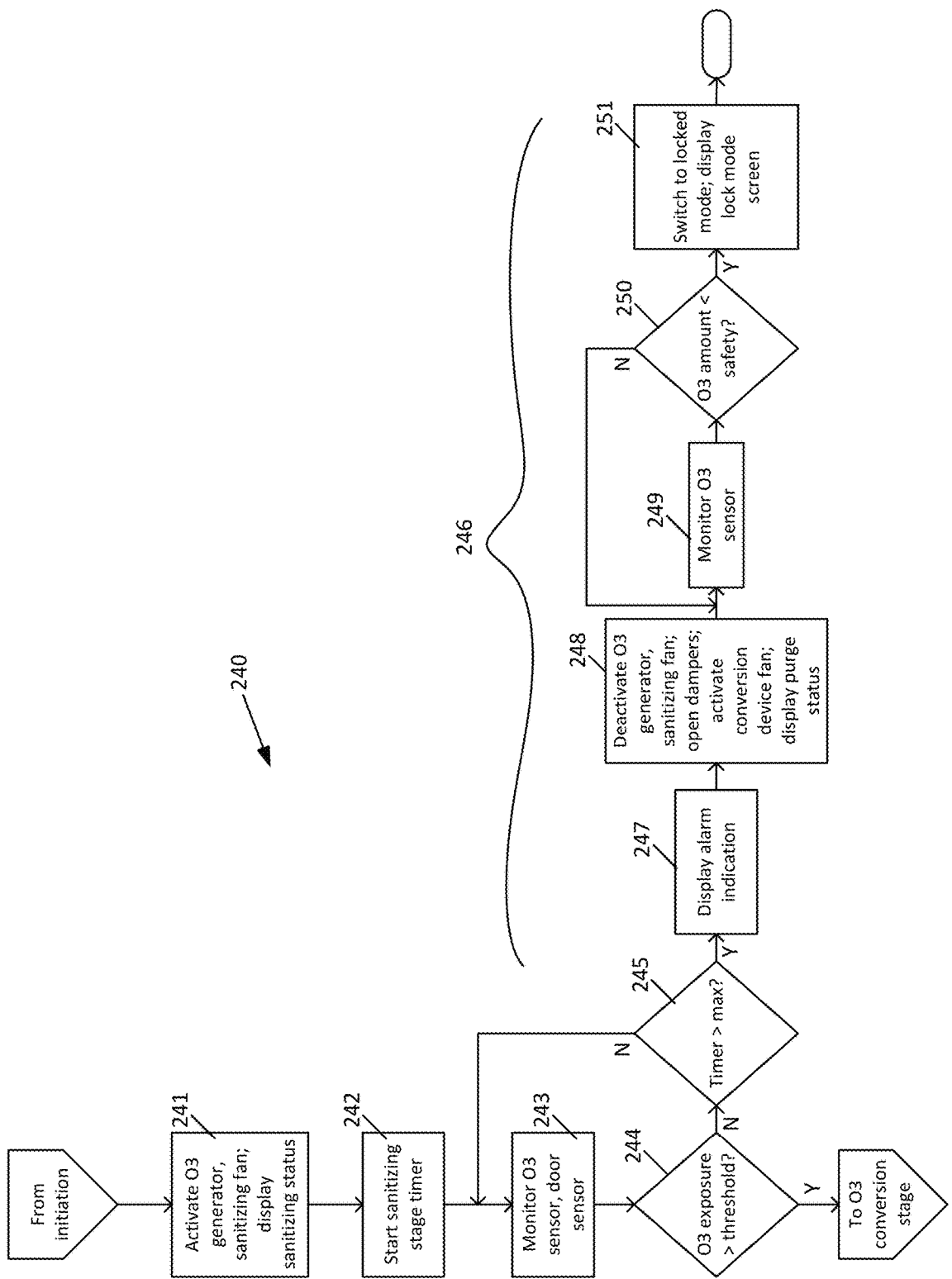
FIG. 17 is a flowchart of a sanitizing stage subroutine of the process of FIG. 15.
Figure 22:
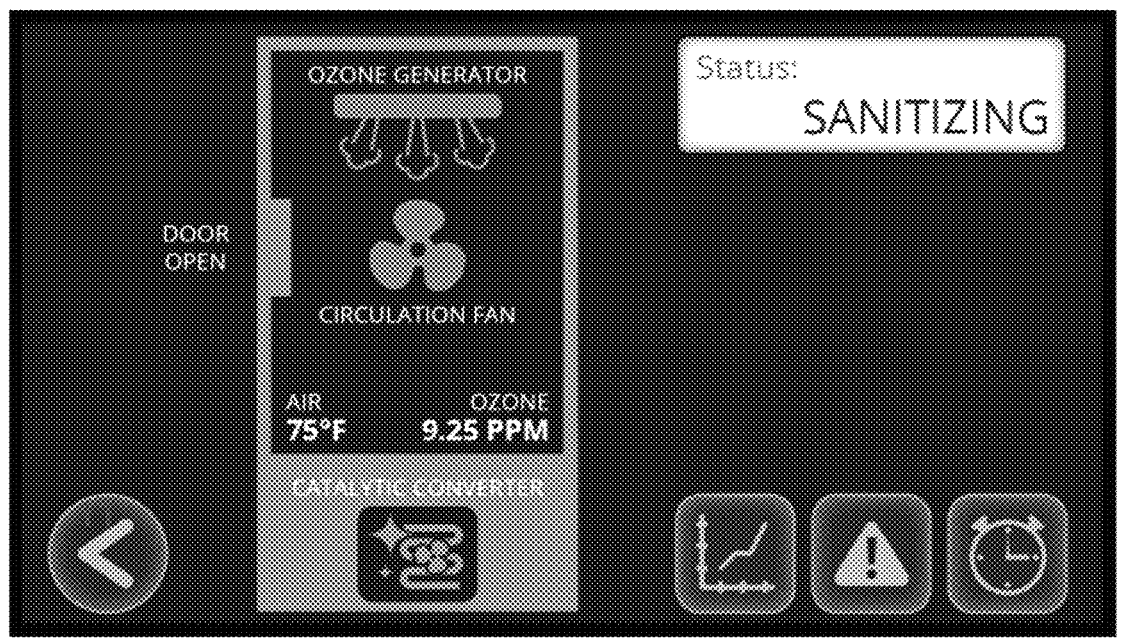
FIG. 22 is an exemplary screenshot of a sanitizing stage status view displayed on the user interface of the sanitizing cabinet system during the sanitizing stage subroutine.

Referring to FIGS. 17 and 22, to begin the sanitizing stage, at step 241, the controller 104 activates the ozone generator 18 and the sanitizing fan 20 and directs the user interface 102 to display a sanitizing status indicator, e.g., the display screen shown in FIG. 22. At step 242, the controller 104 starts a sanitizing stage timer. As will be explained in further detail below, the purpose of the sanitizing stage timer is to enable the controller 104 to determine when the amount of time elapsed during the sanitizing stage 240 exceeds a predetermined maximum sanitizing time threshold indicative that the sanitizing cabinet system may not be sanitizing properly. In certain embodiments the controller can adjust operating levels of the ozone generator 18 and/or sanitizing fan 20 based on feedback from the ozone sensor 56. But in other cases, the controller 104 operates each component at the same operating level for the duration of the selected cycle.

During the cycle, the controller 104 monitors the output of the ozone sensor 56 (step 243) and the door switch 106. The step 243 may broadly be referred to as monitoring the sanitizing cabinet system during the sanitizing cycle. As explained in further detail below, the controller is configured to output one or more alarm indications not represented in FIG. 17 based on this monitoring if, for example, the controller 104 receives a signal from the ozone sensor 56 that the level of ozone inside the sanitizing compartment 14 exceeds a predetermined maximum ozone threshold, the controller receives a signal from the door switch 106 that the door 28 has been opened in spite of the lock 44 in the midst of a sanitizing cycle, etc.

If no such error is detected, the controller 104 typically executes the chosen sanitizing stage to completion. In an exemplary embodiment, the controller 104 is configured to determine stage completion by monitoring the amount of ozone exposure in the sanitizing compartment 14 and comparing it to a predetermined ozone exposure threshold for the respective cycle type (decision point 244). In one or more embodiments, the controller 102 is configured to determine ozone exposure as a function of the ozone concentration with respect to time. The exposure threshold is in units of ozone concentration-time. For example, ozone exposure may be measured as an integral of the ozone concentration signal over time. In a simplified example, for a given cycle, the controller might use a threshold ozone exposure value of 30 PPM-minutes. If the ozone sensor 56 detects a constant ozone concentration in the sanitizing compartment 14 of 6 PPM, the controller 104 would determine that the desired ozone exposure threshold has been reached after a 5-minute duration. Whereas by contrast, if the ozone sensor 56 outputs a signal representative of a constant ozone concentration of 2 PPM, the controller 104 would not determine that the required ozone exposure has been met until the cycle has reached 15 minutes in duration.

Although not shown in FIG. 17, during the sanitizing stage 240, the controller 104 maintains the dampers 62, 62 in the closed positions and keeps the conversion air mover 78 off so that the catalyst 76 is substantially prevented from interacting with or neutralizing any ozone in the sanitizing compartment during this stage.

In the illustrated embodiment, the controller 104 is configured monitor the timer initiated in step 242 to determine when the amount of time elapsed during sanitizing stage exceeds a predetermined maximum sanitizing stage time threshold (decision point 245). If the controller 104 determines that the amount of time elapsed during the sanitizing stage exceeds the predetermined maximum sanitizing stage time threshold, the controller 104 is configured to conduct a sanitize timeout routine 246 in response. In the illustrated embodiment, the sanitize timeout routine 246 comprises displaying an initial alarm indication on the user interface 102 (e.g., a pop-up warning indicating incomplete sanitizing has occurred; step 247). Additionally, at steps 248, the controller deactivates the ozone generator 18 and sanitizing fan 20, opens the dampers 62, 64, activates the conversion air mover 78, and displays a purge status on the display. Thus, the illustrated sanitize timeout routine 246 comprises using the ozone conversion device 22 to neutralize ozone in the sanitizing compartment 14. The controller 104 monitors the output from the ozone sensor 56 (step 249) to determine, at decision point 250, when ozone concentration in the sanitizing compartment falls below a safe ozone concentration level. Subsequently, in the illustrated embodiment, the controller 104 is configured to switch the cabinet from an operating mode to a locked mode, keeping the door lock 44 locked until an administrator provides an unlock command to the controller 104. In one or more embodiments, the administrator can remotely send the unlock command from the remote server 116 to the controller 104 via the transceiver 112. In certain embodiments, the administrator enters administrator-level credentials at the user interface 102 and then locally issues the unlock command.

The purpose of the sanitize timeout routine 246 is to inhibit the sanitizing cabinet system 10 from being used when it may not be properly functioning to sanitize as intended. It is contemplated that the sanitizing cabinet system 10 may be used in the medical field, e.g., for sanitizing medical supplies or devices. In this context, it is important that the sanitizing cabinet system 10 reliably reach the indicated level of sanitizing. A sanitizing stage 240 that takes an excessive amount of time is a leading indicator that the cabinet system 10 may have an unresolved issue rendering it incapable of reaching the indicated levels of sanitizing. When this occurs, the sanitize timeout routine 246 provides a substantial impediment to using the device in its current, potentially ineffective condition.

Figure 18:
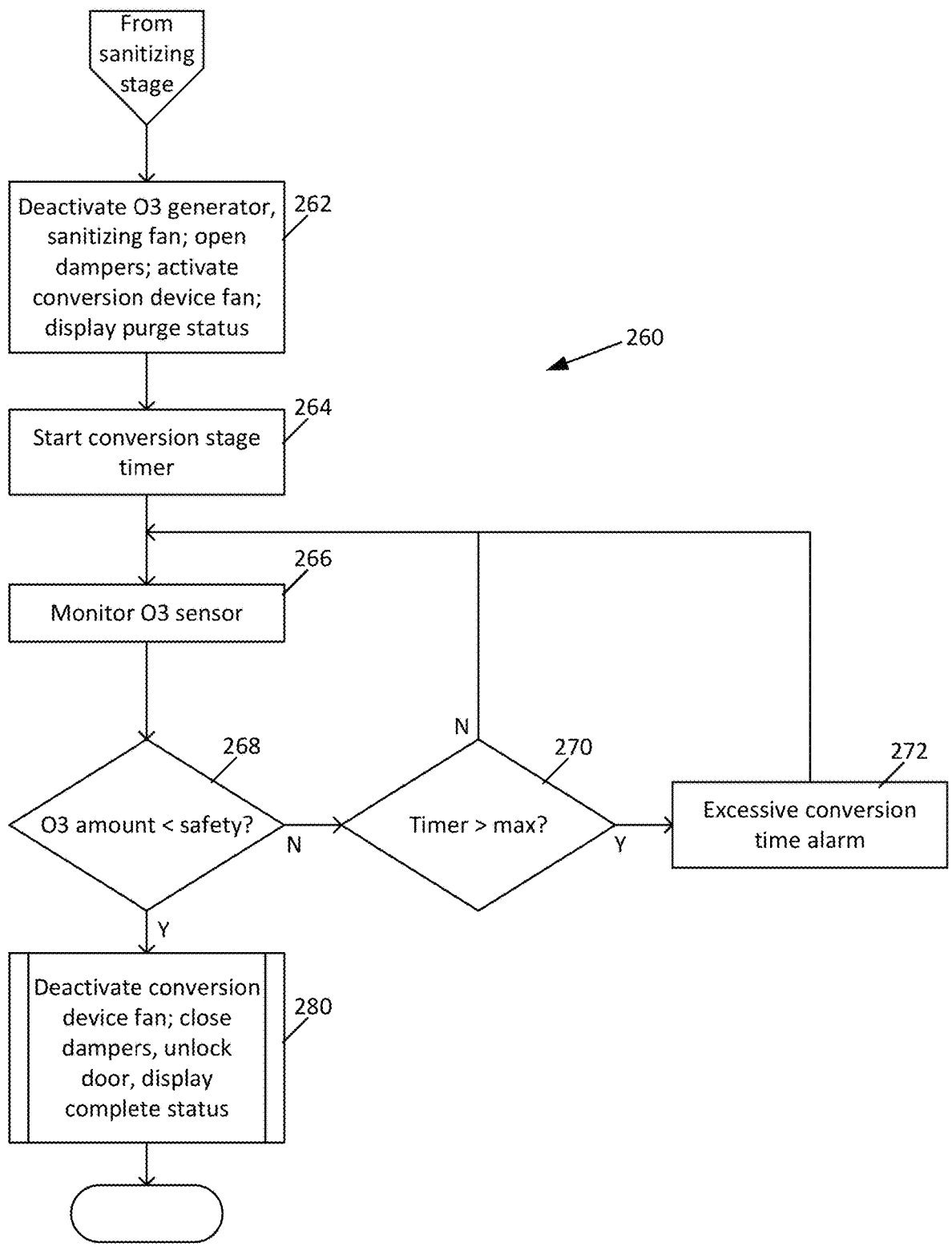
FIG. 18 is a flowchart of an ozone conversion stage subroutine and termination subroutine of the process of FIG. 15.
Figure 23:
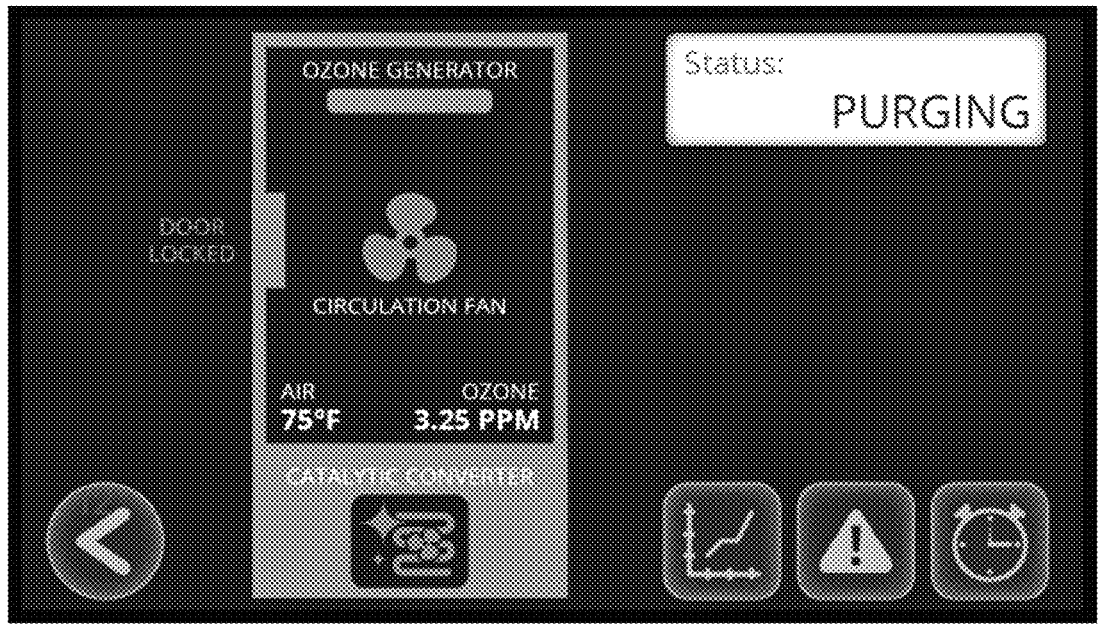
FIG. 23 is an exemplary screenshot of an ozone conversion stage status view displayed on the user interface of the sanitizing cabinet system during the sanitizing stage subroutine.

Referring to FIG. 18, after a successful sanitizing stage 240 is complete, the controller then proceeds to the ozone conversion stage 260. At step 262, the controller 104 deactivates the ozone generator 18 and the sanitizing fan 20 and opens the dampers 62, 64 using the actuators 62B, 64B. In addition, the controller 104 turns on the ozone conversion air mover 78 and directs the user interface 102 to display a purge status indicator, e.g., the display screen shown in FIG. 23. Step 262 recirculates ozonated air from the sanitizing compartment 14 through the catalytic converter 76 to quickly neutralize ozone in the cabinet 12. As in the sanitizing stage 240, the controller 104 is configured to start a conversion stage timer at the beginning of the conversion stage (step 264).

Figure 24:
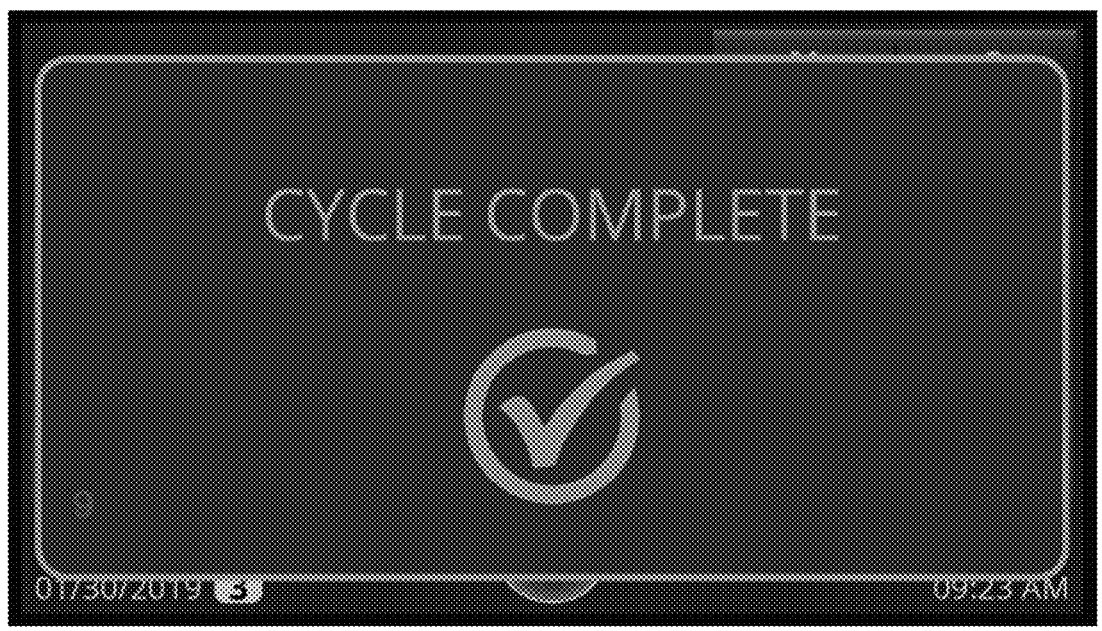
FIG. 24 is an exemplary screenshot of a cycle complete status pop-up displayed on the user interface when a sanitizing cycle is complete.

Throughout the ozone conversion stage, the controller 104 monitors the signal from the ozone sensor 56 (step 266) to determine, at decision point 268, when the concentration of ozone in the sanitizing compartment 14 is less than a predetermined safe ozone concentration threshold, e.g., less than 0.1 ppm or less than 0.05 ppm. In response to determining the concentration of ozone in the sanitizing compartment 14 is less than the predetermined safe ozone concentration threshold, the controller 104 is configured to output a signal indicating that the sanitizing cycle is complete (termination subroutine 280). For example, the controller 104 sends a signal to the door lock 44 to unlock the door 28. Additionally, the controller 104 can send a signal to the user interface 102 to direct the user interface to display an indication of the complete cycle on the display (see FIG. 24).

Thus, it can be seen that, during each of the sanitizing stage 240 and the ozone conversion stage 260, the controller 104 is configured to lock the cabinet 12 in a closed configuration, and in response to determining the concentration of ozone in the sanitizing compartment is less than the predetermined safe ozone concentration threshold, the controller is configured to unlock the cabinet to allow the cabinet to be opened. Upon completion of the cycle, the user may remove the articles from the sanitizing compartment 12B. The sanitizing cabinet system 10 will then be ready for use in another cycle for sanitizing a new set of articles.

As shown at decision point 270 and step 272, the controller 104 is configured to determine an amount of time elapsed during each ozone conversion stage 260 and to determine when the amount of time elapsed during an ozone conversion stage exceeds a predetermined maximum ozone conversion time threshold. The controller 104 is configured to output an excessive ozone conversion time alarm indication (not shown) in response to determining the amount of time elapsed during an ozone conversion stage 260 exceeds the predetermined maximum ozone conversion time threshold. However, the excessive ozone conversion time event does not result in locking out the cabinet system 10 in the illustrated embodiment.

Although not depicted in FIGS. 15-18, during the cycle, the controller 104 is configured to monitor other aspects of the sanitizing cabinet system 10 and output one or more alarm indications based on said monitoring. For example, in one or more embodiments, the controller 104 is configured to display the alarm indications on the display of the user interface 102. In certain embodiments, the controller 104 is configured to log alarm indications in the memory 108 as they occur.

In an exemplary embodiment, the controller 104 is configured to determine based on the signal from the ozone sensor 56 when the ozone concentration inside the sanitizing compartment exceeds a predetermined high ozone concentration threshold. In response to determining based on the signal from the ozone sensor 56 that the ozone concentration inside the sanitizing compartment 14 exceeds the predetermined high ozone concentration threshold, the controller 104 is configured to output an high ozone concentration alarm indication (e.g., direct the user interface 102 to display an indication such as a pop-up message warning about the high ozone concentration, transmit the indication wirelessly to a user mobile (e.g., via SMS notification), or communicate the indication to the user in any other appropriate way.).

In certain embodiments, the controller 104 is configured to determine based on the door sensor 106 and the signal from the ozone sensor 56 that the door 28 is open while the ozone concentration in the sanitizing compartment 14 exceeds a predetermined safe ozone concentration threshold. In response to determining based on the door sensor 106 and the signal from the ozone sensor 56 that the door is open while the ozone concentration inside the sanitizing compartment 14 exceeds the predetermined maximum safe ozone concentration threshold, the controller 104 is configured to output a door open alarm indication (e.g., direct the user interface 102 to display an indication such as a pop-up message warning that the door has opened, transmit the indication wirelessly to a user mobile (e.g., via SMS notification), or communicate the indication to the user in any other appropriate way.).

In certain embodiments, the controller 104 is configured to detect a fault in the ozone sensor 56. For example, the controller can detect that the ozone sensor 56 has become disconnected from the controller 104 such that the controller is no longer receiving signal from the ozone sensor. In one embodiment, when the controller 104 detects the fault in the ozone sensor 56, the controller is configured to output an ozone sensor fault alarm indication (e.g., direct the user interface 102 to display an indication such as a pop-up message regarding the sensor fault, transmit the indication wirelessly to a user mobile (e.g., via SMS notification), or communicate the indication to the user in any other appropriate way.). In certain embodiments, when an ozone sensor fault alarm occurring during a sanitizing cycle, the controller 104 can switch the sanitizing cabinet system 10 to the locked mode as described above with respect to the sanitize timeout routine 246.

Figure 27:
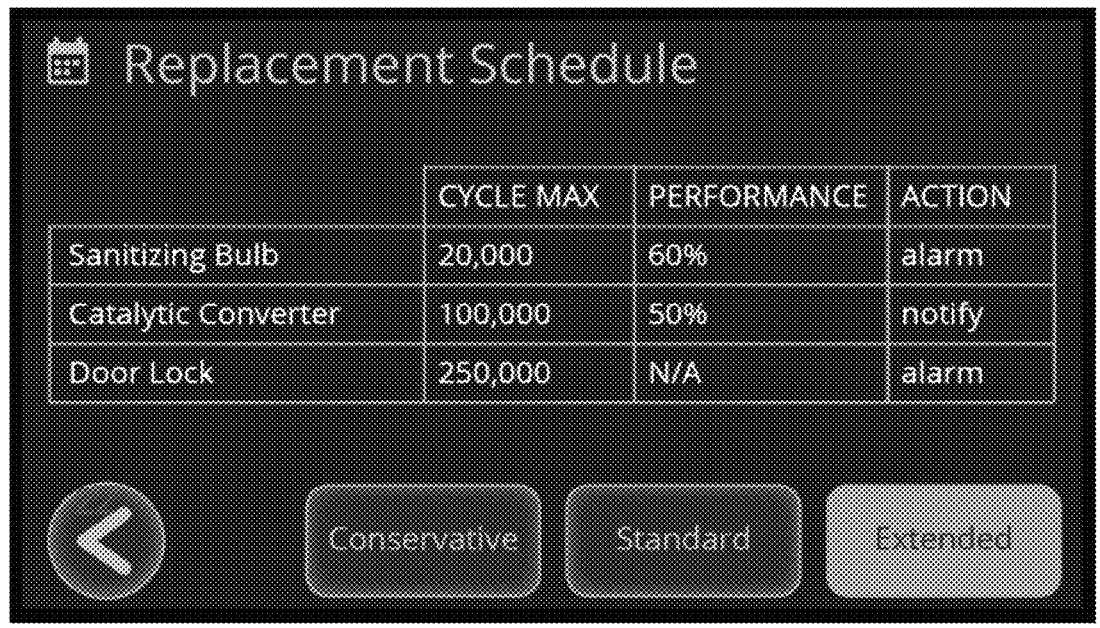
FIG. 27 is an exemplary screenshot of the replacement schedule view in yet another configuration.
Figure 28:
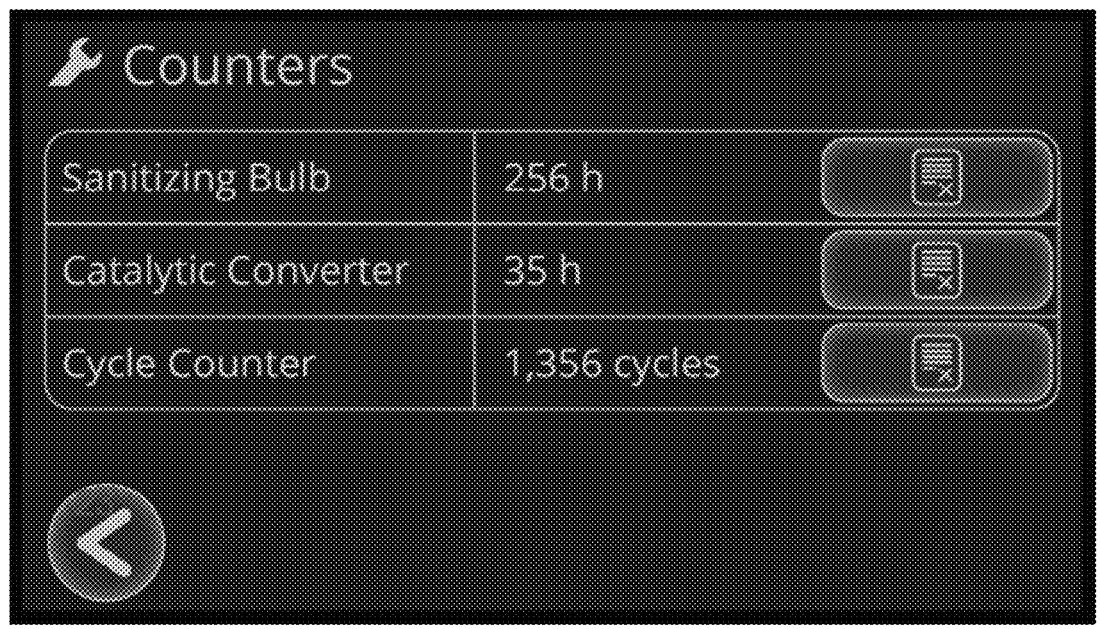
FIG. 28 is an exemplary screenshot of a cycle counter view indicating usage data for each of the expendable parts stored in memory by the control system of the sanitizing cabinet system during use.
Figure 29:
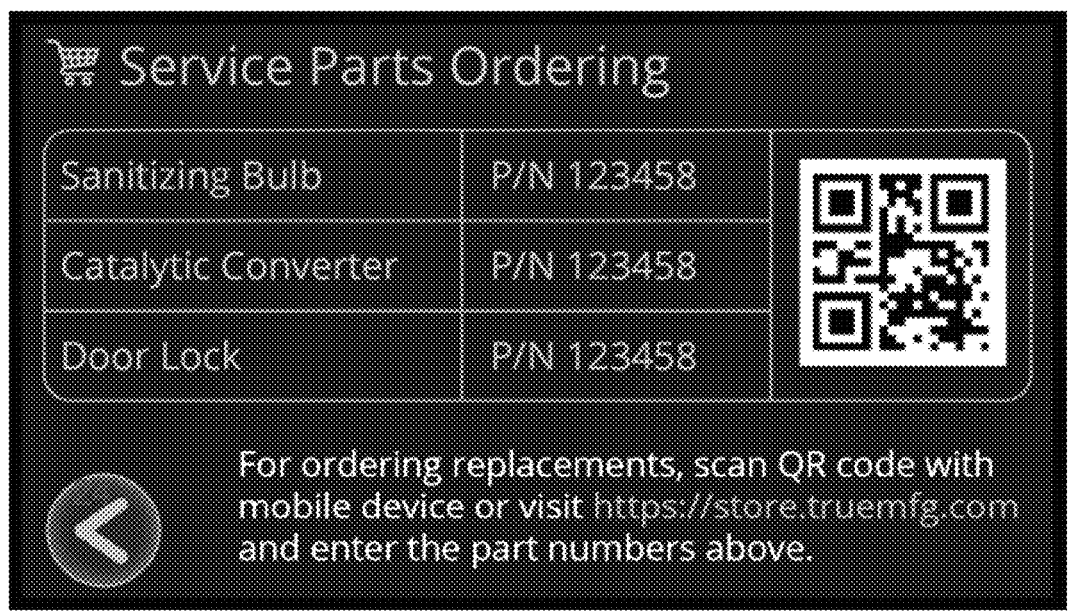
FIG. 29 is an exemplary screenshot of a parts ordering view including a QR code for accessing an e-commerce website from which replacements for the expendable parts can be purchased.

As can be seen in display screens shown in FIGS. 25-28, the illustrated sanitizing cabinet system 10 is generally configured to monitor the usage of certain replaceable, expendable components such as one or more of the sanitizing bulb 18, the ozone conversion catalyst 76, and the door lock 44. In an exemplary embodiment, the controller 104 is configured to store in the memory 108 an indication of the number of sanitizing cycles conducted with each of the expendable parts 18, 76, 44. For each expendable part of interest, the controller 104 is configured to determine based on the number stored in memory that the number of sanitizing cycles conducted with the replaceable, expendable part installed in the sanitizing cabinet system exceeds a predetermined replacement threshold number for the respective part. The controller 104 is configured to output a corresponding replacement alarm indication (e.g., direct the user interface 102 to display an indication such as a pop-up message that part replacement is required, transmit the indication wirelessly to a user mobile (e.g., via SMS notification), or communicate the indication to the user in any other appropriate way.) in response to determining that the number of sanitizing cycles conducted with the expendable part installed in the sanitizing cabinet system exceeds replacement threshold number. Upon replacement of the part, the controller 104 is configured to reset the corresponding cycle count in the memory 108. As shown in FIGS. 25-27, in the illustrated embodiment, the replacement threshold numbers for each of the sanitizing bulb 18, the ozone conversion catalyst 76, and the door lock 44 are user-adjustable, depending on whether the user wants to operate the sanitizing cabinet system in a conservative manner, a standard manner, or a manner that uses each expendable part for as long as reasonably possible before replacement. As shown in FIG. 29, in the illustrated embodiment, the user can call up a display screen on the user interface 102 that displays a QR code for accessing a website from which the user can order replacements for the expendable parts.

In an exemplary embodiment, the controller 104, via the transceiver 112, is configured to send the cycle count information for the expendable components to the remote server 116. For example, the controller 104 can be configured to automatically transmit the cycle count on a periodic basis and/or upon passing a threshold cycle count that is stored in the memory 108. In certain embodiments, the remote server 116 may be configured to remotely and automatically switch the sanitizing cabinet system 10 into a locked mode if the number of cycles of use of an expendable component exceeds a maximum threshold number stored in a memory of the remote server. In the locked mode, the cabinet system 10 may not be used to conduct sanitizing cycles without an administrator first taking action to unlock the device. In certain embodiments, a manufacturer of the cabinet system, a servicer, or other operator or administrator of the cabinet system may maintain the remote server 116 and establish the safe maximum cycle count threshold for each expendable part. The above-described remote locking feature provides the manufacturer, servicer, or operator/administrator a way of ensuring that the cabinet system is never used in a way that is thought to be ineffective.

The controller 104 may also be configured to publish various other information to the remote server 116, such as alarm indications, sanitizing stage and/or ozone conversion stage cycle times, ozone concentration information from sanitizing cycles, etc.

In one or more embodiments, the sanitizing cabinet system 10 includes a light sensor (not shown) in, or otherwise associated with, the ozone generator 17. The light sensor is configured to detect when the generator bulb 18 begins to dim or burn out. When dimming or burn-out is detected, the controller 104 transmits an indication that the bulb should be replaced. For example, the indication may be displayed on the display of the user interface 102, transmitted wirelessly to the user (e.g., via SMS notification), or communicated to the user in any other appropriate way. In certain embodiments, the controller 104 can also adjust the parameters of its sanitization cycles based on the dimming of the internal bulb. For example, as the bulb dims, the controller 104 can increase the duration of each type of sanitization cycle accordingly.

One feature of the illustrated sanitizing cabinet system 10 is that it is readily adaptable from existing cabinet platforms that are in wide commercial circulation during times in which there are no extant pathogenic emergencies. For example, the sanitizing cabinet system 10 can be readily manufactured from a refrigeration cabinet that would typically be used for a refrigeration device. Such devices are widely sold when restaurants and shops are considered safe by ordinary consumers. But when an epidemic occurs, the perceived safety of these types of establishments may decrease, leading to decreased demand for refrigeration devices. In contrast, epidemics also create sharply increased demand for sanitizing devices. Thus, one aspect of this disclosure pertains to adapting inventory of various types of normal, day-to-day cabinet devices for use as sanitizing cabinets during an epidemic or other event that causes increased demand for sanitizing cabinets.

One embodiment of a process for redirecting cabinet inventory within the scope of this disclosure starts with existing cabinet inventory, either fully assembled cabinets or cabinet components. If the cabinets are not fully assembled, the manufacturer first assembles the cabinets from an existing stock of cabinet parts. If the cabinets are fully assembled, it may be necessary to remove existing system components from the assembled cabinet. After obtaining a cabinet shell, the manufacturer must then configure the cabinet for performing sanitizing operations. If the cabinet inventory is for commercial refrigerator cabinets, air distribution passaging and air distribution fans may already be present in the cabinet. If not, the manufacturer can add suitable air flow passaging and one or more fans to serve as the ozone distribution passaging and sanitizing fan. In the illustrated embodiment, the manufacturer mounts an ozone generator 18 on the device, preferably at a position in the air flow passaging so that the sanitizing fan blows or draws (broadly, moves) air across the ozone generator. In certain embodiments, the manufacturer also fluidly connects an ozone conversion device to the cabinet. For example, the ozone conversion device may be mounted to a wall of the cabinet so that the ozone conversion device resides outsize the primary storage compartment which will serve as the sanitizing compartment. In an exemplary embodiment, the manufacture forms a hole (e.g., two holes) in a wall of the storage compartment and mounts the ozone conversion device to the wall outside of the storage compartment and over the hole.

To quickly transition existing cabinet inventory for use as sanitizing cabinet systems, the generator may be configured to generate no more ozone than is permitted by the relevant regulatory agency. This enables the cabinet shells to be put into service as sanitizing cabinets without retrofitting them with complex safety controls. Alternatively, a manufacturer could retrofit cabinet inventory with generators configured to produce greater amounts of ozone, so that the cabinet systems can run faster sanitizing cycles for higher throughput. In that event, the manufacturer may incorporate some or all of the components of the control system 100. At a minimum the manufacturer can equip high-ozone cabinet systems with an automatic door lock and a controller or interlock that is configured to only allow operation the generator when the door lock is in the locked configuration, in order to prevent excessive amounts of ozone from being emitted.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A sanitizing cabinet system comprising:
a cabinet defining a sanitizing compartment;
ozone distribution passaging in open fluid communication with the sanitizing compartment;
an ozone generator in the ozone distribution passaging;
a sanitizing air mover in the ozone distribution passaging configured to move air from the sanitizing compartment across the ozone generator to form ozonated air and to move the ozonated air into the sanitizing compartment; and
an ozone conversion device configured to be selectively opened and closed, the ozone conversion device being configured to neutralize ozone in the sanitizing compartment when opened;
wherein the cabinet comprises an upper portion generally above the sanitizing compartment, a lower portion generally below the sanitizing compartment, and a height extending from the upper portion to the lower portion;

wherein the ozone generator is received the upper portion and the ozone conversion device is received in the lower portion;

wherein the ozone distribution passaging comprises an air mover plenum in which the sanitizing air mover is received, the air mover plenum defining a return air inlet, the air mover plenum extending along the upper portion;

wherein the cabinet comprises a front and a back, the ozone distribution passaging comprising an ozone discharge plenum extending heightwise along the back from the upper portion, the ozone discharge plenum including a front plenum wall, the front plenum wall defining a plurality of orifices spaced apart along the height of the cabinet, the sanitizing cabinet system configured to discharge ozonated air from the ozone discharge plenum directly through the orifices into open space of the sanitizing compartment;

wherein the lower portion of the cabinet is an ozone conversion portion and wherein the cabinet comprises a dividing wall between the sanitizing compartment and the ozone conversion portion, the ozone conversion device being attached to the dividing wall and received in the ozone conversion portion;

wherein the dividing wall comprises an inlet opening and an outlet opening, each of the inlet opening and the outlet opening providing fluid communication between the sanitizing compartment and the ozone conversion device; and wherein the ozone conversion device comprises:
a housing defining an interior space;
first and second dampers in the housing, the first and second dampers being configured to divide the interior space of the housing between an upstream chamber, an ozone conversion chamber, and a downstream chamber, the first and second dampers being configured to be selectively opened and closed, the first and second dampers being configured to fluidly separate the ozone conversion chamber from the upstream chamber and the downstream chamber when closed and configured to provide fluid communication between the ozone conversion chamber and the upstream chamber and the downstream chamber when opened;
ozone conversion catalyst in the ozone conversion chamber; and
an ozone conversion device air mover in the housing, the housing being mounted on the dividing wall of the cabinet such that the upstream chamber fluidly communicates with the inlet opening and the downstream chamber fluidly communicates with the outlet opening.

2. The sanitizing cabinet system as set forth in claim 1, further comprising a controller connected to the ozone conversion device, the sanitizing air mover, and the ozone generator, the controller being configured to control the ozone generator and the ozone conversion device to conduct sanitizing cycles in the cabinet system, each sanitizing cycle comprising a sanitizing stage and a conversion stage; wherein during each sanitizing stage, the controller is configured to activate the ozone generator and close the first and second dampers; wherein during each conversion stage, the controller is configured to deactivate the ozone generator and open the first and second dampers.

3. The sanitizing cabinet system as set forth in claim 2, wherein during each sanitizing stage, the controller is configured to activate the sanitizing air mover and deactivate the ozone conversion device air mover; and wherein during each conversion stage, the controller is configured to activate the ozone conversion device air mover and deactivate the sanitizing air mover.

4. The sanitizing cabinet system as set forth in claim 1, wherein the housing of the ozone conversion device is sealed to the dividing wall and the first and second dampers are configured so that, when the first and second dampers are closed, the ozone conversion chamber is fluidly isolated from the sanitizing compartment.

5. The sanitizing cabinet system as set forth in claim 1, further comprising an ozone sensor configured to output a signal representative of a concentration of ozone in the sanitizing compartment.

6. The sanitizing cabinet system as set forth in claim 5, further comprising a controller connected to the ozone generator and the ozone sensor, the controller configured to execute a sanitizing cycle in which the controller activates the ozone generator until the controller determines, based on an evaluation of the signal from the ozone sensor with respect to time, that an amount of ozone exposure inside the sanitizing compartment has reached an exposure threshold.

7. The sanitizing cabinet system as set forth in claim 6, further comprising:
a door movable relative to the cabinet between an open position and a closed position for selectively opening and closing the sanitizing compartment; and
an automatic door lock for selectively locking and unlocking the door in the closed position.

8. The sanitizing cabinet system as set forth in claim 7, wherein the controller is configured to maintain the ozone generator in an off state unless the automatic door lock locks the door in the closed position.

9. The sanitizing cabinet system as set forth in claim 7, wherein after determining that the amount of ozone exposure inside the sanitizing compartment has reached the exposure threshold, the controller is configured to deactivate the ozone generator and control the door lock to keep the door locked in the closed position until the controller determines, based on the signal from the ozone sensor, that an amount of ozone inside the sanitizing compartment is less than a safe ozone threshold.

10. The sanitizing cabinet system as set forth in claim 6, wherein the controller is configured to determine an amount of time that the ozone generator is activated during each sanitizing cycle.

11. The sanitizing cabinet system as set forth in claim 10, wherein the controller is configured to conduct a sanitize timeout routine in response to the amount of time exceeding a maximum sanitizing time threshold.

12. The sanitizing cabinet system as set forth in claim 11, wherein the sanitize timeout routine comprises deactivating the ozone generator.

13. The sanitizing cabinet system as set forth in claim 12, wherein the sanitize timeout routine further comprises using the ozone conversion device to neutralize ozone in the sanitizing compartment.

14. The sanitizing cabinet system as set forth in claim 11, wherein the sanitize timeout routine further comprises providing a warning indicating incomplete sanitizing.

15. The sanitizing cabinet system as set forth in claim 14, further comprising a display on the cabinet, wherein said providing the warning indicating incomplete sanitizing comprising displaying the warning on the display.

16. The sanitizing cabinet system as set forth in claim 11, wherein the sanitize timeout routine further comprises keeping the cabinet locked until an administrator provides an unlock command to the controller.

17. The sanitizing cabinet system as set forth in claim 1, wherein the sanitizing compartment has an internal volume of greater than 7 cubic feet.

18. The sanitizing cabinet system as set forth in claim 1, wherein the ozone generator comprises a UV light configured to energize components of air moving through the ozone distribution passaging to generate high-energy plasma including ozone.

19. The sanitizing cabinet system as set forth in claim 1, wherein the ozone distribution passaging comprises an upper corner region connecting the air mover plenum and the ozone discharge plenum, the ozone generator being located in said region.

* * * * *